United States Patent
Anderson et al.

(10) Patent No.: US 10,004,724 B2
(45) Date of Patent: Jun. 26, 2018

(54) COMPOUNDS ALPHA V BETA 6 INTEGRIN ANTAGONISTS

(71) Applicant: GlaxoSmithKline Intellectual Property Development Limited, Brentford, Middlesex (GB)

(72) Inventors: Niall Andrew Anderson, Stevenage (GB); Matthew Howard James Campbell-Crawford, Stevenage (GB); Ashley Paul Hancock, Stevenage (GB); Seble Lemma, Stevenage (GB); Simon John Fawcett MacDonald, Stevenage (GB); John Martin Pritchard, Stevenage (GB); Panayiotis Alexandrou Procopiou, Stevenage (GB); Stephen Swanson, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days. days.

(21) Appl. No.: 15/514,414

(22) PCT Filed: Sep. 22, 2015

(86) PCT No.: PCT/EP2015/071798
§ 371 (c)(1),
(2) Date: Mar. 24, 2017

(87) PCT Pub. No.: WO2016/046241
PCT Pub. Date: Mar. 31, 2016

(65) Prior Publication Data
US 2017/0290818 A1   Oct. 12, 2017

(30) Foreign Application Priority Data
Sep. 26, 2014   (GB) .................................. 1417018.7

(51) Int. Cl.
C07D 471/04 (2006.01)
A61K 31/4375 (2006.01)
C07D 207/04 (2006.01)

(52) U.S. Cl.
CPC ........ *A61K 31/4375* (2013.01); *C07D 207/04* (2013.01); *C07D 471/04* (2013.01)

(58) Field of Classification Search
CPC ................................................... C07D 471/04
See application file for complete search history.

(56) References Cited

U.S. PATENT DOCUMENTS 7,632,951 B2   12/2009   Schadt et al.

FOREIGN PATENT DOCUMENTS

| WO | WO 99/30709 A1 | 6/1999 |
|---|---|---|
| WO | WO 99/31061 A1 | 6/1999 |
| WO | WO 00/72801 A2 | 12/2000 |
| WO | WO 00/78317 A1 | 12/2000 |
| WO | WO 01/24797 A1 | 4/2001 |
| WO | WO 01/34602 A2 | 5/2001 |
| WO | WO 01/096334 A2 | 12/2001 |
| WO | WO 02/07730 A1 | 1/2002 |
| WO | WO 02/22616 A2 | 3/2002 |
| WO | WO 02/053099 A2 | 7/2002 |
| WO | WO 02004/058254 A1 | 7/2004 |
| WO | WO 2005/082889 A1 | 9/2005 |
| WO | WO 2008/118455 A1 | 10/2008 |
| WO | WO 2009/055418 A1 | 4/2009 |
| WO | WO 2011/111880 A1 | 9/2011 |
| WO | WO 2014/154725 A1 | 10/2014 |
| WO | WO 2015/048819 A1 | 4/2015 |
| WO | WO 2016/046225 A1 | 3/2016 |
| WO | WO 2016/046226 A1 | 3/2016 |
| WO | WO 2016/046230 | 3/2016 |
| WO | WO 2016/046230 A1 | 3/2016 |
| WO | WO 2016/134223 A2 | 8/2016 |
| WO | WO 2016/145258 A1 | 9/2016 |
| WO | WO 2017/158072 A1 | 9/2017 |
| WO | WO 2017/162570 A1 | 9/2017 |
| WO | WO 2017/162572 A1 | 9/2017 |

OTHER PUBLICATIONS

International Search Report for International Application No. PCT/EP2015/071776, Nov. 5, 2015 (date of completion of the international search).

(Continued)

*Primary Examiner* — Laura L Stockton
(74) *Attorney, Agent, or Firm* — Jane F. Djung; Kathryn A. Lutomski

(57) ABSTRACT

A compound according to formula (I)

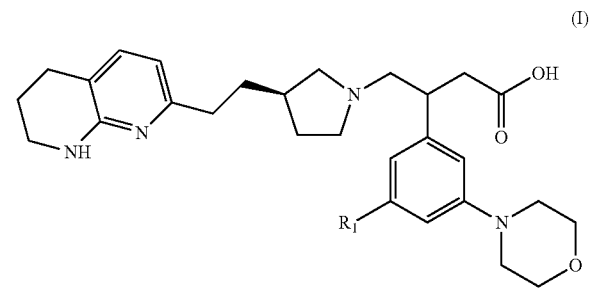

wherein $R_1$ is hydrogen, cyclopropyl, or pyrazolyl, wherein said pyrazolyl is optionally substituted by one or two methyl groups; or a pharmaceutically acceptable salt thereof.

17 Claims, No Drawings

(56) References Cited

OTHER PUBLICATIONS

International Search Report for International Application No. PCT/EP2015/071777, Nov. 20, 2015 (date of completion of the international search).
International Search Report for International Application No. PCT/EP2015/071798, Nov. 4, 2015 (date of completion of the international search).
International Search Report for International Application No. PCT/EP2015/071782, Oct. 21, 2015 (date of completion of the international search).
Cho, et al., "Pirfenidone: an anti-fibrotic and cytoprotective agent as therapy for progressive kidney disease", *Expert Opin. Investig. Drugs*, vol. 19, No. 2, pp. 275-283 (2010).
Goodman et al., "Integrins as therapeutic targets", *Trends in Pharmacological Sciences*, vol. 33, No. 7, pp. 405-412 (2012).
Hahm et al., "avB6 integrin Regulates Renal Fibrosis and Inflammation in Alport Mouse", *The American Journal of Pathology*, vol. 170, No. 1, pp. 110-125 (2007).
Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).
Margadant, C. et al., "Integrin-TGF-β crosstalk in fibrosis, cancer, and wound healing", *EMBO Reports*, vol. 11, No. 2, pp. 97-105 (2010).
Popov et al, "Integrin avB6 is a marker of the progression of biliary and portal liver fibrosis and a novel target for antifibrotic therapies", *Journal of Hepatology*, vol. 48 pp. 453-464 (2008).
Trevillian et al., "αvβ6 integrin expression in diseased and transplanted kidneys", *Kidney International*, vol. 66, pp. 1423-1433 (2004).
Whitman et al., "Nonpeptide αvβ3 antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).
Woodcock, et al. The treatment of idiopathic pulmonary fibrosis, *F1000Prime Reports*, vol. 6, No. 16, pp. 1-9 (2014).
International Search Report for International Application No. PCT/EP2014/056013, dated May 9, 2014, 4 pages.
International Search Report for International Application No. PCT/EP2015/071776, dated Nov. 23, 2015, 4 pages.
International Search Report for International Application No. PCT/EP2015/071777, dated Nov. 26, 2015, 4 pages.
International Search Report for International Application No. PCT/EP2015/071782, dated Nov. 2, 2015, 4 pages.
International Search Report for International application No. PCT/EP2015/071798, dated Nov. 10, 2015, 4 pages.
International Search Report for International application No. PCT/EP2017/056204, dated May 15, 2017, 5 pages.
International Search Report for International application No. PCT/EP2017/056525, dated May 2, 2017, 4 pages.
International Search Report for International application No. PCT/EP2017/056527, dated May 2, 2017, 5 pages.
Restriction Requirement for U.S. Appl. No. 14/778,095, dated Sep. 21, 2016, 9 pages.
Non-Final Office Action for U.S. Appl. No. 14/778,095, dated Mar. 29, 2017, 14 pages.
Notice of Allowance for U.S. Appl. No. 14/778,095, dated Nov. 3, 2017, 11 pages.
Notice of Allowance for U.S. Appl. No. 15/514,407, dated Nov. 6, 2017, 16 pages.
Restriction Requirement for U.S. Appl. No. 15/514,416, dated Aug. 14, 2017, 12 pages.
Non-Final Office Action for U.S. Appl. No. 15/514,416, dated Nov. 2, 2017, 18 pages.
Notice of Allowance for U.S. Appl. No. 15/514,399, dated Dec. 15, 2017, 13 pages.
Notice of Allowance for U.S. Appl. No. 15/514,399, dated Aug. 21, 2017, 11 pages.

COMPOUNDS ALPHA V BETA 6 INTEGRIN ANTAGONISTS

This application is a § 371 of International Application No. PCT/EP2015/071798, filed 22 Sep. 2015, which claims the priority of GB Application No. 1417018.7, filed 26 Sep. 2014.

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, for the use of a compound in the manufacture of a medicament for the treatment of conditions in which an antagonist of $\alpha_v\beta_6$ integrin is indicated and a method for the treatment or prophylaxis of disorders in which antagonism of $\alpha_v\beta_6$ integrin is indicated in a human.

BACKGROUND OF THE INVENTION

Integrin superfamily proteins are heterodimeric cell surface receptors, composed of an alpha and beta subunit. At least 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces. The integrin family can be grouped into sub-families that share similar binding recognition motifs in such ligands. A major subfamily is the RGD-integrins, which recognise ligands that contain an RGD (arginine-glycine-aspartic acid) motif within their protein sequence. There are 8 integrins in this sub-family, namely $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, & $\alpha_v\beta_8$ share a common $\alpha_v$ subunit with a divergent $\beta$ subunit, and $\alpha_v\beta_1$, $\alpha_5\beta_1$ & $\alpha_8\beta_1$ share a common $\beta_1$ subunit with a divergent a subunit. The $\beta_1$ subunit has been shown to pair with 11 different a subunits, of which only the 3 listed above commonly recognise the RGD peptide motif (Humphries et al, *Journal of Cell Science*, 2006, 119, 3901).

The 8 RGD-binding integrins have different binding affinities and specificities for different RGD-containing ligands. Ligands include proteins such as fibronectin, vitronectin, osteopontin, and the latency associated peptides (LAPs) of Transforming Growth Factor $\beta_1$ and $\beta_3$ (TGF$\beta_1$ and TGF$\beta_3$). Integrin binding to the LAPs of TGF$\beta_1$ and TGF$\beta_3$ has been shown in several systems to enable activation of the TGF$\beta_1$ and TGF$\beta_3$ biological activities, and subsequent TGF$\beta$-driven biologies (Worthington et al, *Trends in Biochemical Sciences*, 2011, 36, 47). The diversity of such ligands, coupled with expression patterns of RGD-binding integrins, generates multiple opportunities for disease intervention. Such diseases include fibrotic diseases (Margadant et al, EMBO reports, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect Med.* 2011, 1, a 006478).

A significant number of $\alpha_v$ integrin antagonists (Goodman et al, *Trends in Pharmacological Sciences*, 2012, 33, 405) have been disclosed in the literature including inhibitory antibodies, peptides and small molecules. For antibodies these include the pan-$\alpha_v$ antagonists Intetumumab and Abituzumab (Gras, *Drugs of the Future*, 2015, 40, 97), the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$ and SB-267268 is an example of a compound (Wilkinson-Berka et al, *Invest. Ophthalmol. Vis. Sci.*, 2006, 47, 1600), that inhibits both $\alpha_v\beta_3$ and $\alpha_v\beta_5$. Invention of compounds to act as antagonists of differing combinations of a, integrins enables novel agents to be generated tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a typical survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe.

There are in vitro experimental, animal and IPF patient immunohistochemistry data to support a key role for the epithelially restricted integrin, $\alpha_v\beta_6$, in the activation of TGF$\beta$1. Expression of this integrin is low in normal epithelial tissues and is significantly up-regulated in injured and inflamed epithelia including the activated epithelium in IPF. Targeting this integrin, therefore, reduces the theoretical possibility of interfering with wider TGF$\beta$ homeostatic roles. Partial inhibition of the $\alpha_v\beta_6$ integrin by antibody blockade has been shown to prevent pulmonary fibrosis without exacerbating inflammation (Horan G S et al Partial inhibition of integrin $\alpha_v\beta_6$ prevents pulmonary fibrosis without exacerbating inflammation. *Am J Respir Crit Care Med* 2008 177: 56-65). Outside of pulmonary fibrosis, $\alpha_v\beta_6$ is also considered an important promoter of fibrotic disease of other organs, including liver and kidney (Reviewed in Henderson N C et al Integrin-mediated regulation of TGF$\beta$ in Fibrosis, Biochimica et Biophysica Acta—Molecular Basis of Disease 2013 1832:891-896), suggesting that an $\alpha_v\beta_6$ antagonist could be effective in treating fibrotic diseases in multiple organs.

Consistent with the observation that several RGD-binding integrins can bind to, and activate, TGF$\beta$, different $\alpha_v$ integrins have recently been implicated in fibrotic disease (Henderson N C et al Targeting of $\alpha_v$ integrin identifies a core molecular pathway that regulates fibrosis in several organs *Nature Medicine* 2013 Vol 19, Number 12: 1617-1627; Sarrazy V et al Integrins $\alpha v\beta 5$ and $\alpha v\beta 3$ promote latent TGF-$\beta$1 activation by human cardiac fibroblast contraction *Cardiovasc Res* 2014 102:407-417; Minagawa S et al Selective targeting of TGF-$\beta$ activation to treat fibroinflammatory airway disease *Sci Transl Med* 2014 Vol 6, Issue 241: 1-14; Reed N I et al. The $\alpha_v\beta_1$ integrin plays a critical in vivo role in tissue fibrosis *Sci Transl Med* 2015 Vol 7, Issue 288: 1-8). Therefore inhibitors against specific members of the RGD binding integrin families, or with specific selectivity fingerprints within the RGD binding integrin family, may be effective in treating fibrotic diseases in multiple organs.

SAR relationships of a series of integrin antagonists against $\alpha_v\beta_3$ $\alpha_v\beta_5$, $\alpha_v\beta_6$ and $\alpha_v\beta_8$ have been described (Macdonald, S J F et al. Structure activity relationships of $\alpha_v$ integrin antagonists for pulmonary fibrosis by variation in aryl substituents. *ACS Med Chem Lett* 2014, 5, 1207-1212. 19 Sep. 2014).

It is an object of the invention to provide $\alpha_v\beta_6$ antagonists, preferably with activities against other $\alpha_v$ integrins, such as $\alpha_v\beta_1$, $\alpha_v\beta_3$, $\alpha_v\beta_5$ or $\alpha_v\beta_8$.

BRIEF SUMMARY OF THE INVENTION

In a first aspect of the invention there is provided a compound of formula (I) or a salt thereof, more particularly a pharmaceutically acceptable salt thereof:

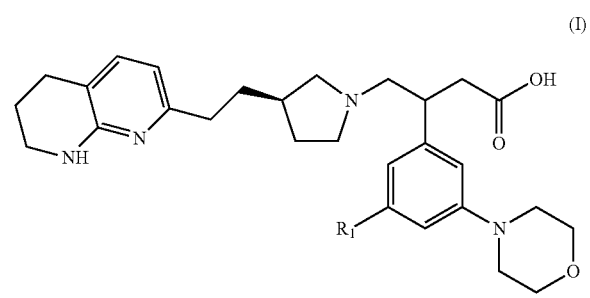

(I)

wherein $R_1$ represents a hydrogen atom, a cyclopropyl group, or a pyrazole ring which pyrazole is optionally substituted by one or two methyl groups.

Compounds of formula (I) and their salts have $\alpha_v\beta_6$ integrin antagonist activity and are believed to be of potential use for the treatment or prophylaxis of certain disorders. The term $\alpha_v\beta_6$ antagonist activity includes $\alpha_v\beta_6$ inhibitor activity herein.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of a disease or condition for which an $\alpha_v\beta_6$ integrin antagonist is indicated.

In a fourth aspect of the present invention, there is provided a method of treatment or prophylaxis of a disease or condition for which an $\alpha_v\beta_6$ integrin antagonist is indicated in a human in need thereof which comprises administering to a human in need thereof a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which an $\alpha_v\beta_6$ integrin antagonist is indicated.

In a sixth aspect of the present invention, there is provided a compound of formula (XV)

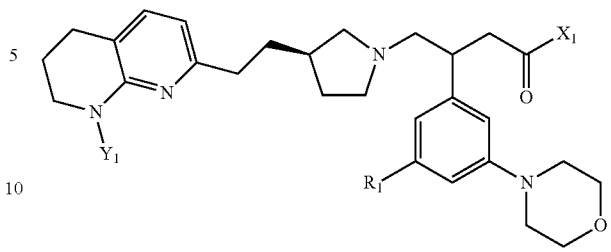

(XV)

wherein $R_1$ is as hereinbefore defined, $X_1$ represents hydroxyl or a moiety which is hydrolysable by metabolism in the human body to form the corresponding acid compound of formula (I) in which $X_1$ is OH;

$Y_1$ represents hydrogen or a moiety which is hydrolysable by metabolism in the human body to form the corresponding amino compound of formula (I) in which $Y_1$ is hydrogen;

provided that when $X_1$ is hydroxyl, then $Y_1$ is not hydrogen.

DETAILED DESCRIPTION OF THE INVENTION

In a first aspect of the invention there is provided a compound of formula (I) or a salt thereof, more particularly a pharmaceutically acceptable salt thereof:

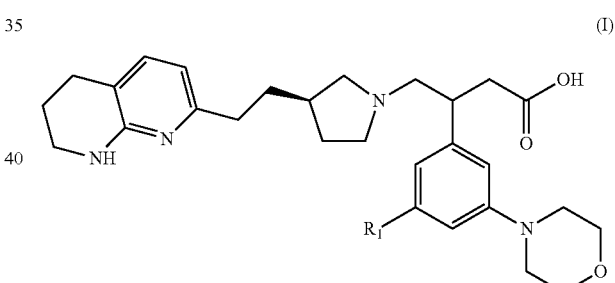

(I)

wherein $R_1$ represents a hydrogen atom, a cyclopropyl group, or a pyrazole ring which pyrazole is optionally substituted by one or two methyl groups.

In some embodiments the compound of formula (I) or a salt thereof has the structural formula (IA):

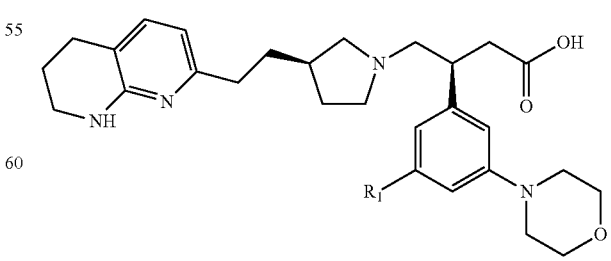

In other embodiments the compound of formula (I) or salt thereof has the structural formula (IB):

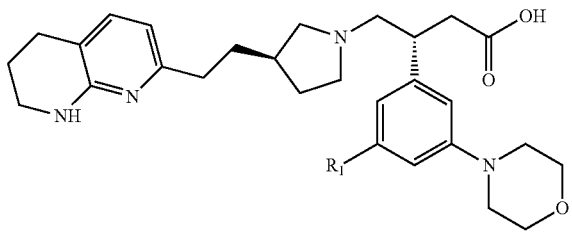

It is to be understood that the present invention covers all combinations of particular and preferred groups described herein.

In some embodiments, $R_1$ represents a hydrogen atom.
In some embodiments, $R_1$ represents a cyclopropyl group.
In some embodiments, $R_1$ represents a 1H-pyrazole ring.
In some embodiments, $R_1$ represents a 3-methyl-1H-pyrazole ring
In some embodiments, $R_1$ represents a 3,5-dimethyl-1H-pyrazole ring In one embodiment the compound is selected from:
(S)-3-(3-morpholinophenyl)-4-((R)-3-(2-(5,6,7,8-tetrahydro-1,8-naphthyridin-2-yl)ethyl)pyrrolidin-1-yl)butanoic acid;
(S)-3-(3-cyclopropyl-5-morpholinophenyl)-4-((R)-3-(2-(5,6,7,8-tetrahydro-1,8-naphthyridin-2-yl)ethyl)pyrrolidin-1-yl)butanoic acid;
(S)-3-(3-morpholino-5-(1H-pyrazol-1-yl)phenyl)-4-((R)-3-(2-(5,6,7,8-tetrahydro-1,8-naphthyridin-2-yl)ethyl)pyrrolidin-1-yl)butanoic acid;
(S)-3-(3-(3-methyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid and
(S)-3-(3-(3,5-dimethyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid or a pharmaceutically acceptable salt thereof.
(S)-3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid
(S)-3-(3-(3-methyl-1H-pyrazol-5-yl)-5-morpholinophenyl)-4-((R)-3-(2-(5,6,7,8-tetrahydro-1,8-naphthyridin-2-yl)ethyl)pyrrolidin-1-yl)butanoic acid
(S)-3-(3-morpholino-5-(1H-pyrazol-4-yl)phenyl)-4-((R)-3-(2-(5,6,7,8-tetrahydro-1,8-naphthyridin-2-yl)ethyl)pyrrolidin-1-yl)butanoic acid.

In one embodiment the compound is:
3-(3-morpholinophenyl)-4-((R)-3-(2-(5,6,7,8-tetrahydro-1,8-naphthyridin-2-yl)ethyl)pyrrolidin-1-yl)butanoic acid, or a pharmaceutically acceptable salt thereof.

Compounds of formula (I) or (IA) or (IB) have both a basic amine group and a carboxylic acid group and can consequently form internal salts, i.e. a zwitterion or inner salts. Therefore, in an embodiment the compound of formula (I) is in a zwitterionic salt form. In another embodiment, the compound of formula (IA) is in a zwitterionic salt form. In another embodiment, the compound of formula (IB) is in a zwitterionic salt form.

It will be appreciated that the present invention covers compounds of formula (I) as the parent compound and as salts thereof, for example as a pharmaceutically acceptable salt thereof. In one embodiment the invention relates to compounds of formula (I) or a pharmaceutically acceptable salt thereof.

For a review on suitable salts see Berge et al., *J. Pharm. Sci.*, 66:1-19, (1977). Suitable pharmaceutically acceptable salts are listed in P H Stahl and C G Wermuth, editors, *Handbook of Pharmaceutical Salts; Properties, Selection and Use*, Weinheim/Zurich: Wiley-VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid. Typically, a pharmaceutically acceptable salt may readily be prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

A pharmaceutically acceptable base addition salt can be formed by reaction of a compound of formula (I) with a suitable organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable inorganic base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine. In one embodiment the compound of formula (I) is in the form of a parent compound.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. It will be appreciated that crystalline forms optionally may be solvated to form, for example, pharmaceutically acceptable solvates, such as hydrates which may be stoichiometric hydrates as well as compounds containing variable amounts of water. Solvates include stoichiometric solvates and non-stoichiometric solvates. Compounds of formula (I) may exist in solvated or non-solvated form.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR)

spectra, Raman spectra, differential scanning calorimetry (DSC), thermogravimetric analysis (TGA) and solid state nuclear magnetic resonance (SSNMR).

The compounds described herein contain two asymmetric centres so that optical isomers, e.g. diastereoisomers and enantiomers may be formed. Accordingly, the present invention encompasses isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

It will be understood by those skilled in the art that certain diastereoisomers may be less active than others and that the activity of an individual diastereoisomer may fall below a selected limit.

In one embodiment, the compound is:

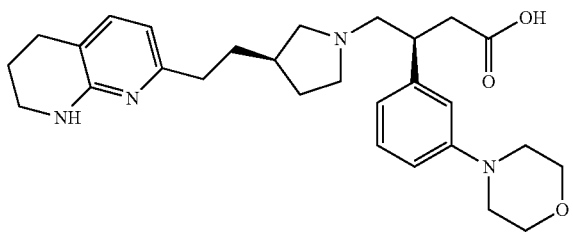 [SMILES: O=C(O)C[C@H](CN1CC[C@@H](CCc2ccc3c(n2)NCCC3)C1)c1cccc(N2CCOCC2)c1]

(S)-3-(3-morpholinophenyl)-4-((R)-3-(2-(5,6,7,8-tetrahydro-1,8-naphthyridin-2-yl)ethyl)pyrrolidin-1-yl)butanoic acid, or a pharmaceutically acceptable salt thereof.

In another embodiment the compound is:

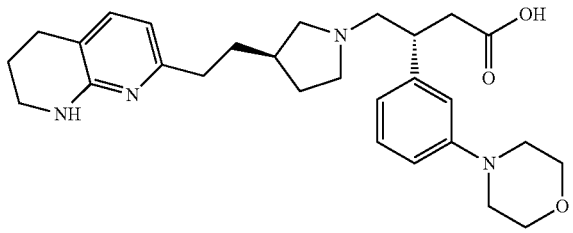 [SMILES: O=C(O)C[C@@H](CN1CC[C@@H](CCc2ccc3c(n2)NCCC3)C1)c1cccc(N2CCOCC2)c1]

(R)-3-(3-morpholinophenyl)-4-((R)-3-(2-(5,6,7,8-tetrahydro-1,8-naphthyridin-2-yl)ethyl)pyrrolidin-1-yl)butanoic acid, or a pharmaceutically acceptable salt thereof.

Separation of isomers may be achieved by conventional techniques known to those skilled in the art, e.g. by fractional crystallisation, chromatography or HPLC.

Compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

In a sixth aspect of the present invention, there is provided a compound of formula (XV

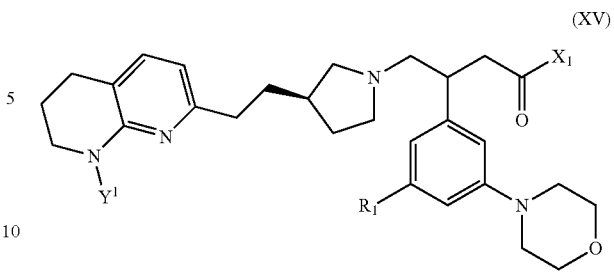

wherein $R_1$ is as hereinbefore defined, $X_1$ represents hydroxyl or a moiety which is hydrolysable by metabolism in the human body to form the corresponding acid compound of formula (I) in which $X_1$ is —OH;

$Y_1$ represents hydrogen or a moiety which is hydrolysable by metabolism in the human body to form the corresponding amino compound of formula (I) in which $Y_1$ is hydrogen;

provided that when $X_1$ is hydroxyl, then $Y_1$ is not hydrogen.

In some embodiments $X_1$ may be a moiety —ORa such that the compound of formula (I) is an ester.

For example the moiety Ra may be selected from $C_{1-6}$ alkyl such as methyl, ethyl, n-propyl, iso-propyl, n-butyl, iso-butyl, sec-butyl, tert-butyl, pentyl (and its isomers) or hexyl (and its isomers); or from $C_{1-6}$ alkoxyalkyl such as 2-methoxyethyl, 2-(tert-butoxy)ethyl; or from $C_{1-6}$ alkylaminoalkyl such as 2-(dimethylamino)ethyl; or from $C_{1-6}$ cyclic carbonate groups such as (5-methyl-2-oxo-1,3-dioxol-4-yl)methyl; or $C_{1-6}$ acyloxyalkyl such as (pivaloyloxy)methyl.

For example the moiety Ra may be selected from aryl groups such as phenyl, 5-indanyl or L-tyrosinyl.

For example the moiety Ra may be selected from groups containing an amino group or an amide group, such as $C_{1-6}$ groups of formula $(CH_2)_n$ NRbRc or $(CH_2)_n$CO NRbRc where n is 1-3 and Ra and Rb are independently H or $C_{1-6}$ alkyl, cycloalkyl, heterocyclyl or Ra and Rb together form a cyclic group such as morpholinyl. Examples of such moieties include dimethylaminoethyl, 2-(4-morpholino)ethyl, amino-2-oxoethyl, and dimethylamino-2-oxoethyl.

For example the moiety Ra may be selected from a hydroxyl containing an alpha-amino acid such as L-serine and L-threonine.

For example the moiety Ra may be a cyclic carbonate of formula:

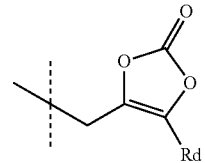

wherein Rd is hydrogen, methyl, ethyl or iso-propyl.

For example, the moiety Ra may be selected from —CHRe-O—CO-Rf in which Re is hydrogen or $C_{1-3}$ alkyl such as methyl, ethyl or iso-propyl, and Rf is $C_{1-4}$ alkyl such as methyl, ethyl, iso-propyl, tert-butyl or $C_{5-6}$ cycloalkyl, or tetrahydropyranyl.

For example, the moiety Ra may be selected from —CH(Rg)-O—CO—O-Ri in which Rg is hydrogen or $C_{1-3}$ alkyl such as methyl, ethyl or iso-propyl, and Ri is $C_{1-4}$ alkyl such as methyl, ethyl, tert-butyl or $C_{5-6}$ cycloalkyl or tetrahydropyranyl.

In some embodiments $X_1$ may be a moiety —NHRj such that the compound of formula (I) is an amide, wherein Rj may for example be $C_{1-6}$ alkyl. For example the compound of formula (I) may be an amide derived from an amino acid linked to the alpha-amino group of the amino acid, e.g. a naturally occurring L-proteinogenic amino acid such as glycine, alanine, phenylalanine, leucine, valine, isoleucine, proline, methionine, cysteine, serine, threonine, histidine, tyrosine, tryptophane, lysine, asparagine, glutamine, glutamic acid, aspartic acid, or arginine, or a di-peptide of the above-mentioned proteinogenic aminoacids. For example Rj may be a proteinogenic amino acid moiety, such as a L-lysine moiety linked to the side-chain epsilon-amino group of the amino acid e.g. —$(CH_2)_4CH(NH_2)CO_2H$.

For example Rj may be a sulfonamide moiety such as —$SO_2$—Rk where Rk is $C_{1-6}$ alkyl, such as methyl, or —NRmRn and Rm and Rn are independently H or $C_{1-6}$ alkyl, cycloalkyl, heterocyclyl or Rm and Rn together form a cyclic group such as morpholinyl.

In some embodiments $Y_1$ may be hydrogen.

In one embodiment (a) $Y_1$ is a $C_{1-6}$ alkyl substituted by a $C_{1-6}$ cyclic carbonate group, for example a (oxodioxolenyl) methyl group such as

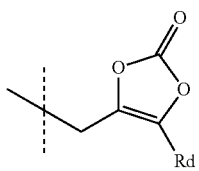

wherein Rk is $C_{1-3}$ alkyl such as methyl, ethyl or iso-propyl.

In another embodiment (b) Y may be a carbamate group, for example

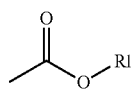

wherein Rl is $C_{1-6}$ alkyl, such as methyl, ethyl, n-propyl, iso-propyl, n-butyl, iso-butyl, n-pentyl, or n-hexyl.

In another embodiment Rl is a $C_{1-6}$ alkyl substituted by a OH or $NMe_2$ group such as —$CH_2CH_2OH$ or —$CH_2CH_2NMe_2$ In another embodiment (c) $Y_1$ may be a group of general structure

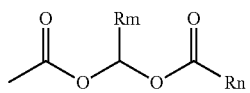

in which Rm is hydrogen, methyl or iso-propyl and Rn is $C_{1-6}$ alkyl, for example methyl, ethyl, iso-propyl, tert-butyl, cycloalkyl for example cyclobutyl, cyclopentyl, cyclohexyl, heterocyclyl for example 4-tetrahydropyranyl, aryl for example phenyl, substituted phenyl, heteroaryl for example 2-, 3- or 4-pyridyl.

In another embodiment (d) $Y_1$ may be a group of general structure

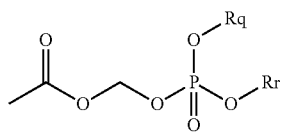

wherein Rq and Rr are independently hydrogen, phenyl, naphthyl, alkyl, $Et_2NCOCH_2$—, or Rq and Rr may form a $C_{1-6}$ ring, such as a saligenin.

In another embodiment compounds of formula (I) are double prodrugs where $X_1$ and $Y_1$ are as defined above in any combination.

The invention relates to all prodrugs of the compounds of formula (I) and pharmaceutically acceptable salts thereof, which upon administration to the recipient are capable of providing (directly or indirectly) a compound of formula (I) or a pharmaceutically acceptable salt thereof, or an active metabolite or residue thereof. Other suitable prodrugs of the compounds of formula (I) are readily apparent to a person skilled in the art (see for instance Burger's Medicinal Chemistry and Drug Discovery, $5^{th}$ Edition, Vol 1: Principles and Practice, and J. Rautio et al (Nature Reviews Drug Discovery 2008, 7, 255-270).

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of structural formula (I) may be prepared by a process involving first deprotection, i.e. cleavage of the ester group, followed optionally by conversion to a salt, of a compound of structural formula (II):

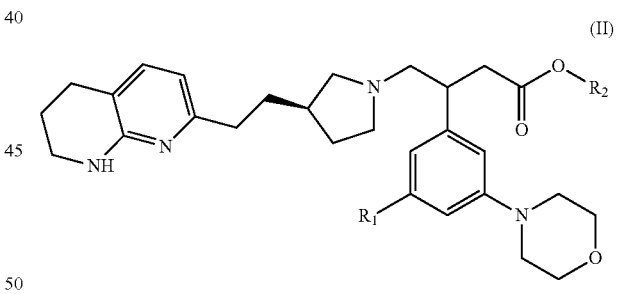

where $R_1$, is as defined above and $R_2$ is a $C_1$ to $C_6$ alkyl group for example tert-butyl, methyl, or a chiral alcohol group such as (–)-menthyl e.g. (1R, 2S, 5R)-2-isopropyl-5-methylcyclohexanol.

The deprotection of compound of structural formula (II) where $R_2$ is tert-Bu may be accomplished by acid hydrolysis using for example hydrochloric, hydrobromic, sulfuric, or trifluoroacetic acid, in an inert solvent, such as dichloromethane, 2-methyl-tetrahydrofuran, tetrahydrofuran, 1,4-dioxane or cyclopentyl methyl ether or water.

After the cleavage of the ester group the resulting product may be converted to the required salt by methods well known to those skilled in the art.

Compounds of structural formula (II) may be obtained by catalytic hydrogenation over a catalyst, such as palladium on carbon, of compounds of structural formula (III):

(III)

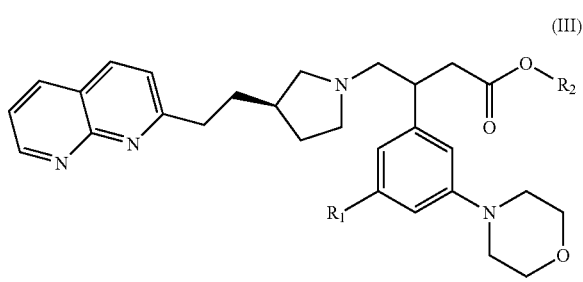

where $R_1$ and $R_2$ are as defined above. The hydrogenation may be carried out at atmospheric pressure, or slightly higher pressure of hydrogen gas, such as 2 to 10 atmospheres, in a suitable solvent such as EtOH, MeOH or a mixture of both.

Compounds of structural formula (III) may be prepared by a process involving reaction of compounds of structural formula (IV):

(IV)

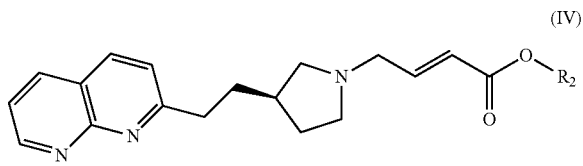

where $R_1$, and $R_2$ are as defined above, and the geometry of the double bond may be (E) or mixture of (E) and (2 isomers, preferably pure (E) isomer with a boronic acid or a boronate ester of structural formula (V):

(V)

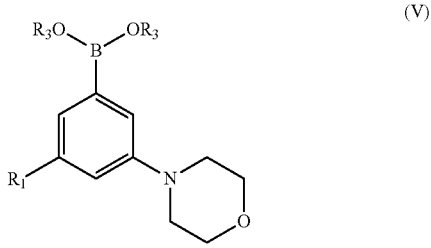

where $R_1$ is as defined above, and $R_3$ represents either hydrogen, or a $C_1$ to $C_6$ alkyl group, such as pinacol in the presence of a suitable catalyst, optionally in the presence of a chiral ligand, at an elevated temperature, and in the presence of a base.

Compounds of structural formula (V) may be used as the pure boronic acid ($R_3$=H), or as boronic acid ester ($R_3$=alkyl group), which may be converted in situ to the boronic acid in the presence of water and a base, such as potassium hydroxide.

The process of condensing compounds of structural formulae (IV) and (V) is performed in the presence of a suitable catalyst, such as a rhodium catalyst, preferably chloro(1,5-cyclooctadiene)rhodium(I) dimer in approximately 5 molar %, in a water-miscible inert solvent, such as 1,4-dioxane, in the presence of base, such as potassium hydroxide, at elevated temperature, such as 50 to 90° C. The condensation process is carried out under strictly anaerobic conditions, where the reaction mixture is purged with an inert gas, such as nitrogen, and evacuated under reduced pressure, repeating the process of evacuation and purging with nitrogen several times, for example three times.

This process produces two diastereoisomers, in approximately 1:1 ratio, which can be separated by crystallisation, chromatography, or by HPLC. The preferred method of separation is chiral HPLC on a chiral support, such as Chiralpak OD-H. The ratio of the diastereoisomers formed can be increased substantially to, for example, greater than 80:20, in the presence of 10% of additives, such as chiral ligands. Such additives include enantiomerically pure phosphine ligands, for example (R)-(+)-2,2'-bis(diphenylphosphino)-1,1'-binaphthalene [(R)-BINAP], which provides as the major isomer the biologically more active diastereoisomer. The configuration at this benzylic asymmetric centre is (S).

The diastereoisomeric ratio was found to be dependent on the size of the alkyl group $R_2$. Thus, when $R_2$ is tertiary, a higher ratio of the desired major isomer was obtained. A more preferred alkyl group $R_2$ is tert-Bu which produced a diastereoisomeric ratio of up to 91:9. The diastereoisomeric ratio can be further increased to, for example greater than 99:1, by chiral HPLC, or by crystallisation.

Compounds of structural formula (IV) can be prepared by reaction of (R)-2-(2-(pyrrolidin-3-yl)ethyl)-1,8-naphthyridine [compound of structural formula (VI)] with a compound of structural formula (VII):

(VI)

(VII)

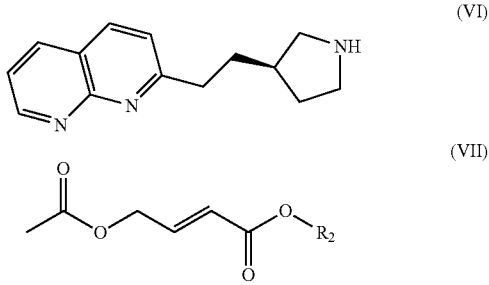

in the presence of approximately 10% of a suitable palladium catalyst, in a suitable inert solvent, such as DCM, in the presence of a tertiary amine base, such as triethylamine, or diisopropylethylamine, and at ambient temperature. Suitable palladium catalysts preferably possess a bidentate ligand, such as two diphenylphosphine groups, for example, 1,1'-bis(diphenylphosphino)ferrocene]dichloropalladium (II) [Pd(dppf)Cl$_2$]. Compound of structural formula (VI) can be used as the free base, or be generated in situ from a salt, such as the dihydrochloride salt, in the presence of a tertiary amine base.

Compound of structural formula (VI) [(R)-2-(2-(pyrrolidin-3-yl)ethyl)-1,8-naphthyridine] may be prepared by methods described herein. By way of illustration (R)-2-(2-(pyrrolidin-3-yl)ethyl)-1,8-naphthyridine can be prepared by methods described in Scheme 1.

Scheme 1

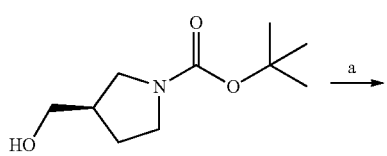

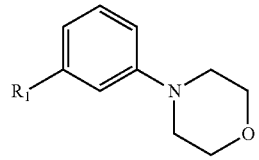

(VIII)

with bis(pinacolato)diboron (available from Aldrich), in the presence of an iridium catalyst, such as methoxy(1,5-cyclooctadiene)iridium (I) dimer, and in the presence of a ligand, such as 4,4'-di-tert-butyl-2,2'-bipyridine, in an inert solvent, such as tert-butyl methyl ether, and at an elevated temperature, such as at about 80° C., preferably in a microwave oven.

Compounds of structural formula (VIII) where R₁ is a cyclopropyl group may be prepared from 1,3-dibromobenzene by the synthetic route outlined in Scheme 3 and by the methods described herein in the experimental section.

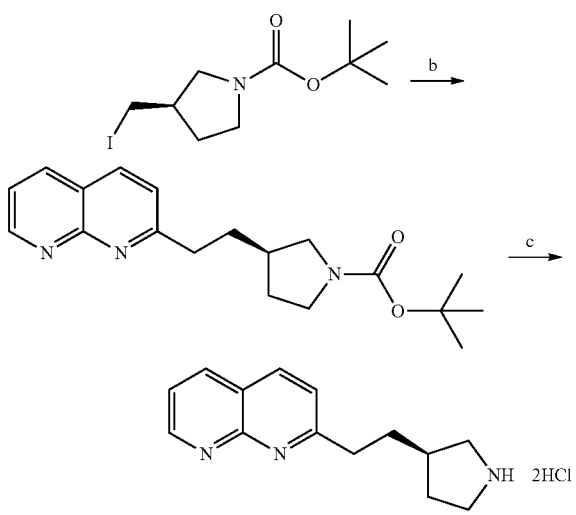

Reagents and conditions: (a) iodine, imidazole, triphenylphosphine, DCM, 0° C.; (b) 2-methyl-[1,8]-naphthyridine, LiN(TMS)₂, THF, 0° C.; (c) 4M HCl in dioxane.

(R)-tert-butyl 3-(hydroxymethyl)pyrrolidine-1-carboxylate is commercially available from Fluorochem, or BePharm Ltd, and 2-methyl-[1,8]-naphthyridine is commercially available, for example, from Manchester Organics Ltd, Aldrich, or Alfa Aesar.

Compound of structural formula (VII) may be prepared by methods described herein. By way of illustration compound of structural formula (VII), where R₂ is tert-butyl, and the double bond having the (E) geometry, may be prepared by the method described in Scheme 2.

Scheme 3

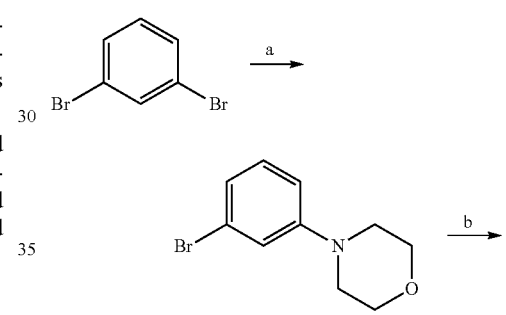

Scheme 2

[structures shown]

Reagents and conditions: (a) isobutylene, conc. H₂SO₄, diethyl ether, 24 h; (b) potassium acetate, acetonitrile, 60° C., 4 h.

(E)-4-Bromobut-2-enoic acid was prepared according to literature procedure [T. Den Hartog, D. J. Van Dijken, A. J. Minnaard, B. L. Feringa *Tetrahedron: Asymmetry* 2010, 21, 1574-1584].

A compound of structural formula (V) where R₁ is H, for example (3-morpholinophenyl)boronic acid, is commercially available from Combi-Blocks Inc.

Compounds of structural formula (V) where R₁ is a cyclopropyl group and R₃ is pinacol can be prepared by reaction of compounds of structural formula (VIII):

Reagents and conditions: (a) Morpholine, Pd₂(dba)₃, NaOBu-t, BINAP, toluene, microwave oven, 50° C.; (b) cyclopropylmagnesium bromide in THF, PdCl₂(dppf)—CH₂Cl₂ adduct, 70° C.

Compounds of structural formula (V) where R₁ is 1H-pyrazole may be prepared from 1,3-dibromo-5-iodobenzene by the synthetic route outlined in Scheme 4 and by the methods described herein in the experimental section.

Scheme 4

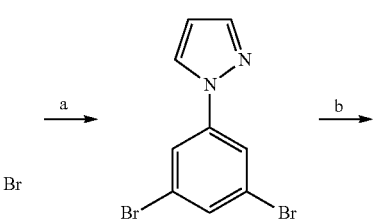

15
-continued

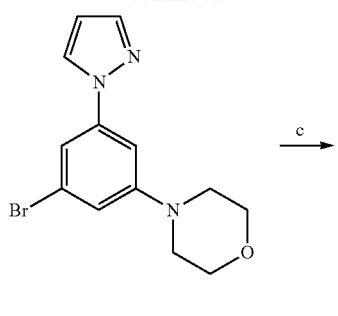

c →

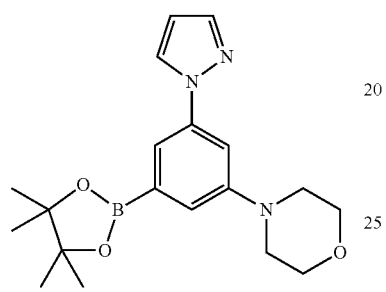

Reagents and conditions: (a) 1H-pyrazole, Cs₂CO₃, CuI, acetonitrile, reflux; (b) morpholine, Pd₂(dba)₃, NaOBu-t, BINAP, toluene, microwave oven, 90° C.; (c) 4,4,4′,4′,5,5,5′,5′-octamethyl-2,2′-bi(1,3,2-dioxaborolane), PdCl₂(dppf), KOAc, DMF, microwave oven, 115° C., 1 h Compounds of structural formula (V) where R₁ is 3-methyl-1H-pyrazole may be prepared from 1,3-dibromo-5-iodobenzene by the synthetic route outlined in Scheme 5 and by the methods described herein in the experimental section.

Scheme 5

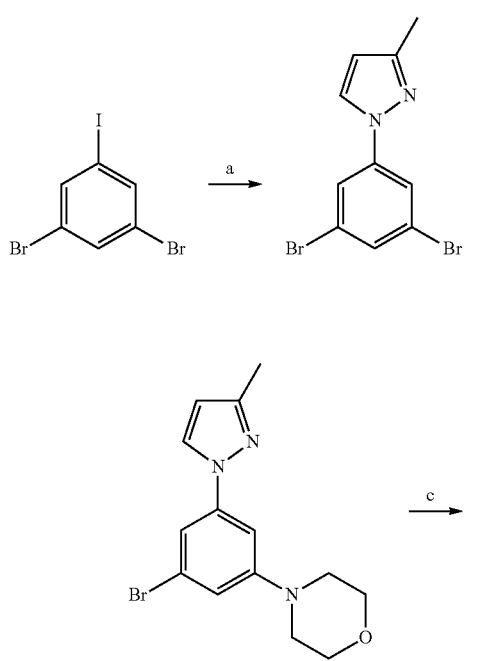

16
-continued

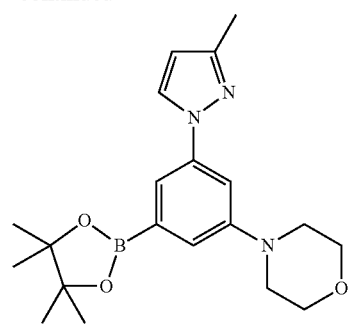

Reagents and conditions: (a) 3-methyl-1H-pyrazole, Cs₂CO₃, CuI, acetonitrile, reflux; (b) morpholine, Pd₂(dba)₃, NaOBu-t, BINAP, toluene, reflux; (c) 4,4,4′,4′,5,5,5′,5′-octamethyl-2,2′-bi(1,3,2-dioxaborolane), PdCl₂(dppf), KOAc, DMF, microwave oven, 115° C., 1 h.

Compounds of structural formula (V) where R₁ is 3,5-dimethyl-1H-pyrazole may be prepared from 1,3-dibromoaniline by the synthetic route outlined in Scheme 6 and by the methods described herein in the experimental section.

Scheme 6

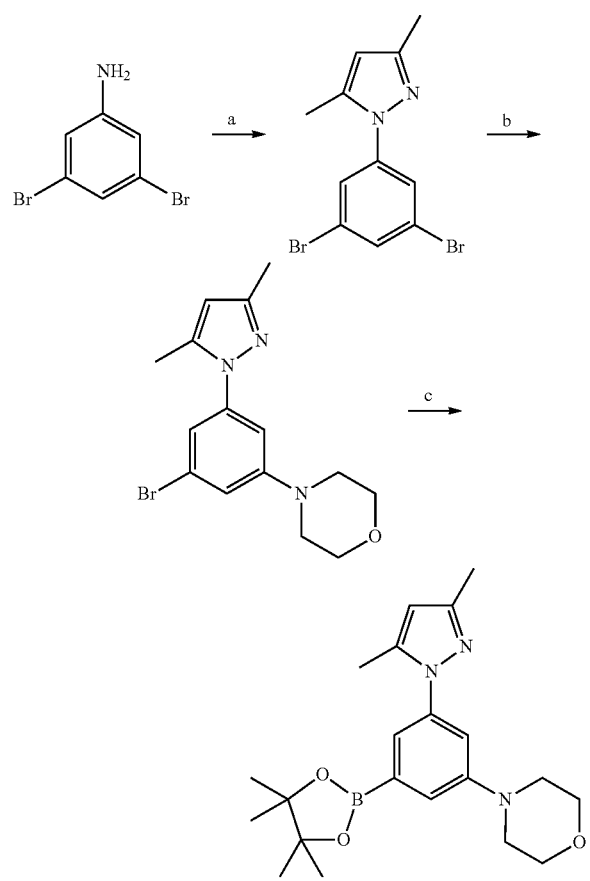

Reagents and conditions: (a) i) sodium nitrite, sulfuric acid, water, 0° C.; ii) (R)-5-((S)-1,2-dihydroxyethyl)-3,4-dihydroxyfuran-2(5H)-one, water; iii) pentane-2,4-dione, 80° C.; (b) morpholine, Pd₂(dba)₃, NaOBu-t, BINAP, toluene, reflux; (c) 4,4,4′,4′,5,5,5′,5′-octamethyl-2,2′-bi(1,3,2-dioxaborolane), PdCl₂(dppf), X-PHOS, KOAc, 1,4-dioxane, 110° C., 1 h. The sequence of carrying out synthetic steps may be altered, for example, the hydrogenation step to form the tetrahydronaphthyridine ring may be carried out at an earlier stage rather than at the penultimate stage.

In an alternative synthetic route compounds of structural formula (II) may be prepared by a Suzuki coupling of compound of structural formula (IX):

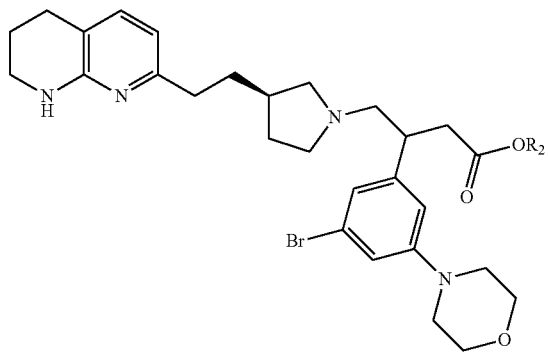

(IX)

where $R_2$ is as defined previously, with an appropriate pyrazoleboronic acid or an ester, such as pinacol ester (available from, for example, Aldrich or ChemBridge) using a suitable catalyst, such as 2'-(dimethylamino)-2-biphenylyl-palladium (II) chloride dinorbornylphosphine complex (available from Aldrich) in the presence of aqueous tripotassium phosphate in a solvent such as ethanol and at an elevated temperature for example about 130° C. preferably in a microwave reactor. This route has been investigated with compounds where $R_1$ is a C-linked pyrazole or substituted pyrazole, such as 1H-pyrazol-5-yl or 3-methyl-1H-pyrazol-5-yl ring. When $R_2$ is methyl the ester group of (II) may hydrolyse under the reaction conditions and provide (I) directly without the need to isolate (II).

Compounds of structural formula (IX) may be prepared from compounds of structural formula (X):

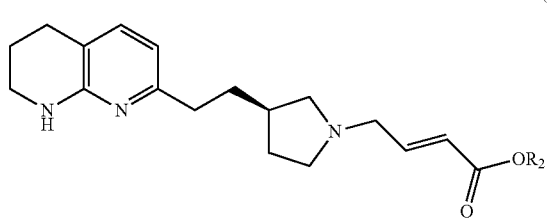

(X)

by reaction with compound of structural formula (XI):

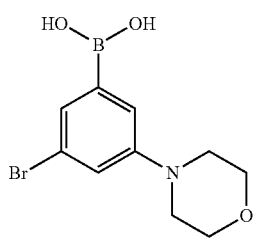

(XI)

3-bromo-5-morpholinophenylboronic acid (available from CombiBlocks) or an appropriate boronic ester, such as a pinacol ester, and in the presence of an appropriate catalyst such as chloro(1,5-cyclooctadiene)rhodium(I) dimer (available from Aldrich), in the presence of a chiral ligand, such as (R)-BINAP (available from Aldrich)) and in the presence of base, such as aqueous KOH, in an inert solvent, such as 1,4-dioxane, at an elevated temperature, for example about 75° C., and under an inert atmosphere such as nitrogen.

The reaction in the absence of the chiral ligand provides a 1:1 mixture of diastereoisomers at the newly generated benzylic chiral centre. The isomers may be separated by chromatography such as preparative chiral HPLC. The presence of (R)-BINAP increases the ratio of the isomers to >80:20 in favour of the required diastereoisomer. The isomers can be separated by chiral HPLC on a column such as Chiralcel OJ H.

Compounds of structural formula (X) can be prepared from compound of structural formula (XII):

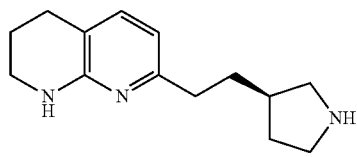

(XII)

either by reaction with a compound of formula (VII), in the presence of approximately 10% of a suitable palladium catalyst, in a suitable inert solvent, such as DCM, in the presence of a tertiary amine base, such as triethylamine, or diisopropylethylamine, and at ambient temperature. Suitable palladium catalysts include for example, 1, 1'-bis (diphenylphosphino) ferrocene] dichloropalladium (II) [Pd (dppf) Cl2]. Compound of structural formula (XII) can be used as the free base, or be generated in situ from a salt, such as the dihydrochloride salt, in the presence of a tertiary amine base. Alternatively the alkylation of compound of structural formula (XII) can be performed using an appropriate bromide, such as (XIII):

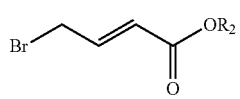

(XIII)

in the presence of a tertiary organic base, such as diisopropylethylamine, or triethylamine in an inert solvent, such as dichloromethane and at a reduced temperature, such as 0° C. Compounds of structural formula (XIII) are either commercially available, for example when $R_2$ is methyl (E)-methyl 4-bromobut-2-enoate is available from Aldrich or when $R_2$ is tert-butyl can be synthesised by the method outlined in Scheme 2.

Compound of structural formula (XII) can be prepared from compound of structural formula (XIV):

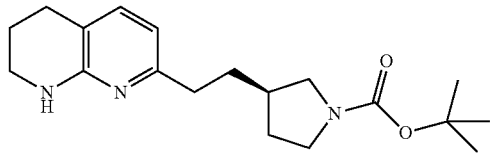

(XIV)

by treatment with an acid, such as HCl in dioxane or TFA in dichloromethane.

Compound of structural formula (XIV) can be prepared from compound of structural formula (XV) by selective catalytic hydrogenation over a catalyst such as Pd on C or Rh on C preferably Rh on Carbon in an inert solvent such as ethyl acetate.

Compounds of structural formula (XV) where $Y_1$ is hydrogen and $X_1$ is alkoxy may be prepared from a compound of formula (I) by reaction with an appropriate alcohol in the presence of HATU and an organic base such as diisopropylethylamine in dichloromethane. The resulting ester may optionally be converted to a salt, such as 4-toluenesulfonate, by reacting with one equivalent of acid.

It will be appreciated that in any of the routes described above it may be advantageous to protect one or more functional groups. Examples of protecting groups and the means for their removal can be found in T. W. Greene Protective Groups in Organic Synthesis' (3rd edition, 3. Wiley and Sons, 1999). Suitable amine protecting groups include acyl (e.g. acetyl, carbamate (e.g. 2', 2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

The absolute configuration of compound (I) may be obtained following an independent enantioselective asymmetric synthesis from an intermediate of known absolute configuration. Alternatively enantiomerically pure compound (I) may be converted into a compound whose absolute configuration is known. In either case comparison of spectroscopic data, optical rotation and retention times on analytical chiral HPLC may be used to confirm absolute configuration. A third option, where feasible, is determination of absolute configuration from an X-ray crystal structure.

Certain compounds of formulae (II) to (XIV) are also believed to be novel and therefore form a yet further aspect of the invention.

Methods of Use

The compounds of formula (I) and salts thereof are believed to have $\alpha_v$ integrin antagonist activity, particularly $\alpha_v\beta_6$ receptor activity, and thus have potential utility in the treatment of diseases or conditions for which an $\alpha_v\beta_6$ antagonist is indicated.

The present invention thus provides a compound of formula (I) or a pharmaceutically acceptable salt thereof for use in therapy. The compound of formula (I) or pharmaceutically acceptable salt thereof can be for use in the treatment of a disease or condition for which an $\alpha_v\beta_6$ integrin antagonist is indicated.

The present invention thus provides a compound of formula (I) or a pharmaceutically acceptable salt thereof for use in the treatment of a disease or condition for which an $\alpha_v\beta_6$ integrin antagonist is indicated.

Also provided is the use of a compound of formula (I) or a pharmaceutically acceptable salt thereof in the manufacture of a medicament for the treatment of a disease or condition for which an $\alpha_v\beta_6$ integrin antagonist is indicated.

Also provided is a method of treating a disease or conditions for which an $\alpha_v\beta_6$ integrin antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Fibrotic diseases involve the formation of excess fibrous connective tissue in an organ or tissue in a reparative or reactive process. $\alpha_v\beta_6$ antagonists are believed to be useful in the treatment of a variety of such diseases or conditions including those dependent on $\alpha_v\beta_6$ integrin function and on activation of transforming growth factor beta via alpha v integrins. Diseases may include but are not limited to pulmonary fibrosis (e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, ARDS associated fibrosis, acute lung injury, radiation-induced fibrosis, familial pulmonary fibrosis, pulmonary hypertension); renal fibrosis (diabetic nephropathy, IgA nephropathy, lupus nephritis, focal segmental glomerulosclerosis (FSGS), transplant nephropathy, autoimmune nephropathy, drug-induced nephropathy, hypertension-related nephropathy, nephrogenic systemic fibrosis); liver fibrosis (virally-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection. There may be additional benefits for additional inhibition of $\alpha_v\beta_1$, $\alpha_v\beta_5$ or $\alpha_v\beta_8$ integrins In addition, pre-cancerous lesions or cancers associated with $\alpha_v\beta_6$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ antagonist is indicated", is intended to include any or all of the above disease states.

In one embodiment the disease or condition for which an $\alpha_v\beta_6$ antagonist is indicated is idiopathic pulmonary fibrosis.

In another embodiment the disease or condition for which an $\alpha_v\beta_6$ antagonist is indicated is selected from corneal scarring, corneal injury and corneal wound healing.

Compositions

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts are as described above. The carrier(s), diluent(s) or excipient(s) must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Further provided is a pharmaceutical composition for the treatment of diseases or conditions for which an $\alpha_v\beta_6$ integrin antagonist is indicated comprising a compound of formula (I) or a pharmaceutically acceptable salt thereof.

Further provided is a pharmaceutical composition comprising 0.01 to 3000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The compounds of this invention can be administered as topical eye drops. The compounds of this invention can be administered via sub-conjunctival, intracameral or intravitreal routes which would necessitate administration intervals that are longer than daily.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers and a carrier or diluent that has a time delay property. Representative examples of biodegradable compositions can include albumin, gelatin, starch, cellulose, dextrans, polysaccharides, poly (D, L-lactide), poly (D, L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions, gels or dry powders.

For compositions suitable and/or adapted for inhaled administration, it is preferred that the compound of the invention is in a particle-size-reduced form, and more preferably the size-reduced form is obtained or obtainable by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The compounds of the invention may be formulated for inhaled or intranasal administration as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

Compositions for inhaled or intranasal administration may also be administered to the lung and other regions of the respiratory tract by nebulisation. Such compositions may be aqueous solutions or suspensions. Solutions for inhalation by nebulisation may be formulated with the addition of agents such as acid or alkali, buffer salts, isotonicity adjusting agents, surfactants or antimicrobials, such as benzylalkonium chloride (BAC). The composition may be sterile and free of antimicrobial preservative. They may be sterilised, for example, by filtration or heating in an autoclave. They may be presented as a non-sterile solution. A single unit dose of a therapeutically effective amount of the compound of the present invention may be provided as a pre-mixed, premeasured formulation, in a single container.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. The compositions may be presented in unitdose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, 0.1 to 2000 mg, or more typically 0.5 to 1000 mg of a compound of the invention calculated as the parent compound.

Each dosage unit for nasal or inhaled administration preferably contains from 0.001 to 50 mg, more preferably 0.01 to 5 mg, yet more preferably 10 to 50 mg, of a compound of the formula (I) or a pharmaceutically acceptable salt thereof, calculated as the free base.

For administration of a nebulised solution or suspension, a dosage unit typically contains from 1 to 15 mg, for example, from 2 mg to 10 mg, or from 4 mg to 6 mg, which may suitably be delivered once daily, twice daily or more than twice daily. The compound of the present invention may be provided in a dry or lyophilised powder for reconstitution in the pharmacy or by the patient, or may, for example, be provided in an aqueous saline solution.

Each dosage unit for nasal or inhaled administration preferably contains from 0.001 to 50 mg, more preferably 0.01 to 50 mg, yet more preferably 10 to 50 mg, of a compound of the formula (I) or a pharmaceutically acceptable salt thereof, calculated as the free base.

The pharmaceutically acceptable compounds of the invention can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 50 mg per day, or 10 to 50 mg, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof may be determined as a proportion of the effective amount of the compound of formula (I) per se.

The compounds of the invention may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetic ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DP1 antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18), receptor therapies (such as etanercept and similar agents); antigen non-specific immunotherapies (such as interferon or other cytokines/chemokines, cytokine/chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-αvβx antibodies and drugs (such as anti-αvβ6 monoclonal antibodies such as those described in WO2003100033A2 may be used in combination, intetumumab, cilengitide) may be used in combination.

Therapies for obstructive airway diseases include bronchodilators such as short-acting β2-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis®, Avastin®, and Aflibercept and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel®, calf blood extract, Levofloxacin®, and Ofloxacin®.

The compounds and compositions of the invention may be used to treat cancers alone or in combination with cancer therapies including chemotherapy, radiotherapy, targeted agents, immunotherapy and cell or gene therapy.

It will be clear to a person skilled in the art that, where appropriate, the other therapeutic ingredient(s) may be used in the form of salts, for example as alkali metal or amine salts or as add addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

The present inventions will now be illustrated by way of example only.

Abbreviations

The following list provides definitions of certain abbreviations as used herein. It will be appreciated that the list is not exhaustive, but the meaning of those abbreviations not herein below defined will be readily apparent to those skilled in the art.
Ac (acetyl)
BCECF-AM (2', 7'-bis-(2-carboxyethyl)-5-(and-6)-carboxyfluorescein acetoxymethyl ester)
BEH (Ethylene Bridged Hybrid Technology)bis(pinacolato) diboron=4,4,4',4',5,5,5',5'-octamethyl-2,2'-bi(1,3,2-dioxaborolane)
Bu (butyl)
CHAPS (3-[(3-Cholamidopropyl) dimethylammonio]-1-propanesulfonate)
Chiralcel OD-H (cellulose tris (3, 5-dimethylphenylcarbamate) coated on 5 μm silica gel)
Chiralpak AD-H (amylose tris (3, 5-dimethylphenylcarbamate) coated on 5 μm silica gel)
Chiralpak ID (amylose tris (3-chlorophenylcarbamate) immobilised on 5 μm silica gel)
Chiralpak AS (amylose tris ((S)-alpha-methylbenzylcarbamate) coated on 5 μm silica gel)
CSH (Charged Surface Hybrid Technology)
CV (column volume)
DCM (dichloromethane)
DMF (N, N-dimethylformamide)
DMSO (dimethylsulfoxide)
Et (ethyl)
EtOH (ethanol)
EtOAc (ethyl acetate)
h (hour/hours)
HATU ((1-[Bis (dimethylamino) methylene]-1H-1, 2, 3-triazolo [4, 5-b] pyridinium 3-oxid hexafluorophosphate)
HCl (Hydrochloric acid)
MDAP (mass directed auto-preparative HPLC)
Me (methyl)
MeOH (methanol)
min minute/minutes
Pd(dppf)Cl$_2$ (1,1'-[bis(diphenylphosphino)ferrocene]dichloropalladium (II))
Ph (phenyl)
$^i$Pr (isopropyl)
(R)-BINAP (R)-(+)-2,2'-Bis (diphenylphosphino)-1,1'-binaphthalene
Si (Silica)
SPE (solid phase extraction)
TBME (tert-butyl methyl ether)
TEA (triethylamine)
TFA (trifluoroacetic acid)
THF (tetrahydrofuran)
TLC (thin layer chromatography)
UPLC (Ultra Performance Liquid Chromatography)
References to brine refer to a saturated aqueous solution of sodium chloride.

EXPERIMENTAL DETAILS

Analytical LCMS
Analytical LCMS was conducted on one of the following systems A, B or C.
The UV detection to all systems was an averaged signal from wavelength of 220 nm to 350 nm and mass spectra were recorded on a mass spectrometer using alternate-scan positive and negative mode electrospray ionization.
LCMS purity is derived from diode array detection.
Experimental details of LCMS systems A-E as referred to herein are as follows:
System A
Column: 50 mm×2.1 mm ID, 1.7 μm Acquity UPLC BEH C$_{18}$ column
Flow Rate: 1 mL/min.
Temp.: 40° C.

Solvents: A: 10 mM ammonium bicarbonate in water adjusted to pH10 with ammonia solution.
B: Acetonitrile
Gradient:

| Time (min) | A % | B % |
|---|---|---|
| 0 | 99 | 1 |
| 1.5 | 3 | 97 |
| 1.9 | 3 | 97 |
| 2.0 | 99 | 1 |

System B
Column: 50 mm×2.1 mm ID, 1.7 μm Acquity UPLC BEH $C_{18}$
Flow Rate: 1 mL/min.
Temp.: 40° C.
Solvents: A: 0.1% v/v solution of trifluoroacetic acid in water
B: 0.1% v/v solution of trifluoroacetic acid in acetonitrile
Gradient:

| Time (min) | A % | B % |
|---|---|---|
| 0 | 97 | 3 |
| 1.5 | 0 | 100 |
| 1.9 | 0 | 100 |
| 2.0 | 97 | 3 |

System C
Column: 50 mm×2.1 mm ID, 1.7 μm Acquity UPLC BEH C18 column
Flow Rate: 1 mL/min
Temp.: 40° C.
Solvents: A: 0.1% v/v solution of formic acid in water
B: 0.1% v/v solution of formic acid in acetonitrile
Gradient:

| Time (min) | A % | B % |
|---|---|---|
| 0 | 97 | 3 |
| 1.5 | 0 | 100 |
| 1.9 | 0 | 100 |
| 2.0 | 97 | 3 |

System D
Column: 50 mm×2.1 mm ID, 1.7 μm Acquity UPLC CSH C18 column
Flow Rate: 1 mL/min.
Temp.: 40° C.
Solvents: A: 10 mM ammonium bicarbonate in water adjusted to pH10 with ammonia solution
B: Acetonitrile
Gradient:

| Time (min) | A % | B % |
|---|---|---|
| 0 | 97 | 3 |
| 1.5 | 5 | 95 |
| 1.9 | 5 | 95 |
| 2.0 | 97 | 3 |

System E
Column: 50 mm×2.1 mm ID, 1.7 μm Acquity UPLC CSH C18 column
Flow Rate: 1 mL/min.
Temp.: 40° C.
Solvents: A: 0.1% v/v solution of formic acid in water
B: 0.1% v/v formic acid in acetonitrile
Gradient:

| Time (min) | A % | B % |
|---|---|---|
| 0 | 97 | 3 |
| 1.5 | 5 | 95 |
| 1.9 | 5 | 95 |
| 2.0 | 97 | 3 |

Mass Directed Auto-Preparative HPLC

Crude products were purified by MDAP HPLC by one of the following methods A-C. The run time was 15 min unless otherwise stated. The UV detection for all methods was an averaged signal from wavelength of 210 nm to 350 nm and mass spectra were recorded on a mass spectrometer using alternate-scan positive and negative mode electrospray ionization.

Method A:

Method A was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

Method B:

Method B was conducted on an XBridge $C_{18}$ column (typically 100 mm×30 mm i.d. 5 μm packing diameter) at ambient temperature. The solvents employed were:
A=10 mM aqueous ammonium bicarbonate adjusted to pH 10 with ammonia solution.
B=acetonitrile.
The gradient employed was:

| Time (min) | Flow Rate (mL/min) | % A | % B |
|---|---|---|---|
| 0 | 40 | 85 | 15 |
| 1 | 40 | 85 | 15 |
| 20 | 40 | 45 | 55 |
| 21 | 40 | 1 | 99 |
| 25 | 40 | 1 | 99 |

Preparation of Intermediates

Intermediate 1: (R)-tert-Butyl 3-(2-(1, 8-naphthyridin-2-yl) ethyl) pyrrolidine-1-carboxylate A 5 L vacuum-jacketed glass reaction vessel (Radley's LARA) was charged with DCM (2 L), followed by triphenylphosphine (339 g, 1.29 mol) and imidazole (88 g, 1.29 mol), and the temperature was reduced to 0° C. Iodine (328 g, 1.29 mol) was then added portionwise over 30 min whilst maintaining the reaction temperature at between 0-5° C. to control the exotherm. During the addition, a thick brown precipitate formed. The precipitate was allowed to warm to room temperature over 15 min and was then stirred at room temperature for a further 30 min. A solution of (R)-tert-butyl 3-(hydroxymethyl) pyrrolidine-1-carboxylate (200 g, 994 mmol) (available from Fluorochem or BePharm Ltd) in DCM (200 mL) was added portionwise over 15 min, whilst maintaining the reaction temperature between 24-30° C. The reaction mixture was stirred for 2 h, then diluted with TBME (8 L), and filtered. The filtrate was concentrated under reduced pressure, and the residue (700 g) was triturated in diethyl ether (2 L) in an ice-water bath to give 333 g of crude product. A 27 g portion of the crude product was purified by chromatography on a silica cartridge (100 g) eluting with a gradient of 0-50% ethyl acetate-cyclohexane over 30 min. The appropriate fractions were combined and evaporated in vacuo to give the title compound (16.33 g, 5%) as a yellow oil. The remaining crude material (~306 g) was purified by chromatography on a silica cartridge (1.5 kg) eluting with a gradient of 0-30% ethyl acetate-cyclohexane over 9.5 column volumes. The appropriate fractions were combined and evaporated in vacuo to give the title compound (233.94 g, 76%) as a pale yellow oil: LCMS (System A) RT=1.19 min, 100%, ES+ve m/z 312 (M+H)$^+$; $[\alpha]_D^{20}$=+23 (c 1.00 in EtOH).

Intermediate 2: (R)-tert-Butyl 3-(2-(1, 8-naphthyridin-2-yl) ethyl) pyrrolidine-1-carboxylate A stirred solution of 2-methyl-1,8-naphthyridine (57.5 g, 399 mmol) (available from Manchester Organics) and (R)-tert-butyl 3-(iodomethyl)pyrrolidine-1-carboxylate (124.2 g, 399 mmol) (Intermediate 1) in THF (1 L) was cooled to 0° C. and treated under nitrogen with a solution of lithium bis(trimethylsilyl)amide in THF (1M, 399 mL, 399 mmol) over 20 min and the reaction mixture was stirred at 0° C. for 3 h. The reaction was quenched with saturated ammonium chloride solution (500 mL) and water (500 mL) and ethyl acetate (1 L) was added. The layers were separated and the aqueous phase was extracted with further ethyl acetate (1 L). The combined organic layers were dried (MgSO$_4$), filtered and evaporated in vacuo. The residual brown oil (162 g) was purified by chromatography on a silica cartridge (750 g) eluting with a gradient of 0-100% [ethyl acetate in (5% MeOH-95% ethyl acetate)] over 8 column volumes. The appropriate fractions were combined and evaporated in vacuo to give the title compound (46.65 g, 36%) as an orange solid: LCMS (System A) RT=0.99 min, 97%, ES+ve m/z 328 (M+H)$^+$, $[\alpha]_D^{20}$+22 (c 1.00 in EtOH).

Intermediate 3: (R)-2-(2-(Pyrrolidin-3-yl) ethyl)-1, 8-naphthyridine, dihydrochloride salt A solution of (R)-tert-butyl 3-(2-(1, 8-naphthyridin-2-yl) ethyl) 34yrrolidone-1-carboxylate (104.71 g, 320 mmol) in DCM (500 mL) was treated slowly with HCl (4M in 1, 4-dioxane (200 mL, 800 mmol) at room temperature. The mixture was stirred overnight at room temperature, by which time a large solid clump had formed in the flask. MeOH (~100 mL) was added to help dissolve the solid and stirring was continued. The LCMS indicated ~72% product and ~25% starting material. Additional quantity of 4M HCl in 1, 4-dioxane (100 mL) was added and stirring was continued for 1 h. The solvent was evaporated in vacuo to give the title compound (89.66 g, 93%) as a purple coloured solid: LCMS (System B) RT=0.34 min, 100%, ES+ve m/z 228 (M+H)$^+$.

Intermediate 4: (E)-tert-Butyl 4-bromobut-2-enoate

Isobutylene gas (363 mL, 3.82 mol) was bubbled through a stirred solution of (E)-4-bromobut-2-enoic acid (210 g, 1.27 mmol) [T. Den Hartog, D. J. Van Dijken, A. J. Minnaard, B. L. Feringa *Tetrahedron Asymmet*. 2010, 21, 1574-1584] and concentrated H$_2$SO$_4$ (20.35 mL, 382 mmol) in diethyl ether (1 L) at −40° C. for 30 min in a steal autoclave. The mixture was sealed in the autoclave and the mixture was stirred at room temperature for 24 h. The reaction was cooled to 0° C. then basified with triethylamine (250 mL) and extracted with DCM (3×200 mL). The organic layer was dried and concentrated in vacuo. The residue was triturated in n-pentane (200 mL) to give the title compound (140 g, 50%) as brown syrup: $^1$H NMR δ (CDCl$_3$, 400 MHz) 6.89 (dt, J=15, 7.5 Hz, 1H), 5.95 (dt, J=15, 1 Hz, 1H), 3.99 (dd, J=7.5, 1 Hz, 2H), 1.48 (s, 9H). The aqueous layer was acidified with 2M HCl to pH 2, and extracted with EtOAc (2×250 mL), the combined organic layers were washed with water (2×500 mL), dried over Na$_2$SO$_4$, evaporated in vacuo to afford unreacted starting material (50 g) as an off-white solid.

Intermediate 5: (E)-tert-Butyl 4-acetoxybut-2-enoate

A stirred solution of (E)-tert-butyl 4-bromobut-2-enoate (280 g, 1.27 mol) in acetonitrile (1.2 L) was treated with potassium acetate (186 g, 1.9 mol) at room temperature. The mixture was stirred at 60° C. for 4 h and the reaction was monitored by TLC (10% diethyl ether in petroleum ether, R$_f$=0.4, detection by UV). The reaction mixture was cooled to room temperature; the solid was removed by filtration and washed with diethyl ether (600 mL). The filtrate was concentrated under reduced pressure, and the residue was purified by flash column chromatography on silica gel eluting with 10% diethyl ether in petroleum ether. Appropriate fractions were combined and evaporated to give the title compound (148 g, 58% yield) as a pale yellow liquid: $^1$H NMR δ (CDCl$_3$, 400 MHz) 6.82 (dt, J=15.5, 5 Hz, 1H), 5.94 (dt, J=15.5, 2 Hz, 1H), 4.71 (dd, J=5, 2 Hz, 2H), 2.11 (s, 3H), 1.49 (s, 9H).

Intermediate 6: (R, E)-tert-Butyl 4-(3-(2-(1, 8-naphthyridin-2-yl) ethyl) pyrrolidin-1-yl) but-2-enoate A mixture of (E)-tert-butyl 4-acetoxybut-2-enoate (Intermediate 5) (14.20 g, 70.9 mmol) and 1,1'-bis(diphenylphosphino)ferrocene]dichloropalladium(II) [Pd(dppf)Cl$_2$] (4.72 g, 6.45 mmol) in DCM (100 mL) was stirred for 15 min under nitrogen before a solution of (R)-2-(2-(pyrrolidin-3-yl)ethyl)-1,8-naphthyridine dihydrochloride (Intermediate 3) (17 g, 57 mmol) in diisopropylethylamine (56.3 mL, 322 mmol) and DCM (200 mL) was added. A clear red solution was obtained which was stirred under nitrogen for 24 hours. The mixture was partitioned between DCM and water (3×170 mL). The organic phase was passed through a phase-separator cartridge and the filtrate was concentrated under reduced pressure. The residual oil (27 g) was loaded in DCM to an aminopropyl cartridge (900 g) and purified by chromatography on CombiFlash Companion XL using a gradient of 0-100% ethyl acetate cyclohexane over 10 column volumes. The appropriate fractions were combined and evaporated in vacuo to give the title compound (17.62 g, 85%) as a brown oil, which solidified on standing: LCMS (System A) RT=1.05 min, 100%; ES+ve m/z 368 (M+H)$^+$.

Intermediate 7: (S)-tert-Butyl 4-((R)-3-(2-(1, 8-naphthyridin-2-yl) ethyl) pyrrolidin-1-yl)-3-(3-morpholinophenyl) butanoate A solution of (3-morpholinophenyl) boronic acid (available from Combi-Blocks Inc.) (6.42 g, 31.0 mmol) in KOH (3.8M, 8.16 mL, 31.0 mmol) was treated with a solution of (R,E)-tert-butyl 4-(3-(2-(1,8-naphthyridin-2-yl)ethyl)pyrrolidin-1-yl)but-2-enoate (Intermediate 6) (6.7 g, 15.5 mmol) in 1,4-dioxane (70 mL) and degassed by evacuation under reduced pressure and nitrogen purging for 5 min. To this was added chloro (1, 5-cyclooctadiene) rhodium (I) dimer (0.382 g, 0.775 mmol) and (R)-BINAP (0.965 g, 1.55 mmol) and the mixture was degassed for a further 5 min. The solution was heated at 90° C. for 60 min. After cooling, the reaction mixture was partitioned between DCM and water. The aqueous phase was extracted with DCM and the combined DCM extracts were evaporated in vacuo. The residual dark brown oil (11.6 g) was purified by chromatography on an aminopropyl cartridge (50 g) eluting with a gradient of 0-50% ethyl acetate-cyclohexane over 40 min. The appropriate fractions were combined and evaporated in vacuo to give 5.61 g of brown oil. Analytical chiral HPLC on Chiralpak AD-H column (250 mm×4.6 mm) eluting isocratically with 50% EtOH (containing 0.2% isopropylamine) heptane, flow rate=1.0 mL/min, detecting at 215 nm indicated the oil was a mixture of two diastereoisomers: Peak 1 RT=6.99 min, 91%; Peak 2 RT=12.2 min, 9%. The mixture was separated by chiral preparative HPLC on a Chiralpak AD-H column (30 mm×250 mm), eluting with 40% ethanol (containing 0.2% isopropylamine) heptanes, flow rate=30 mL/min, detecting at 230 nm, collecting fractions of the major component (RT=6.5-10 min). The combined fractions were evaporated under reduced pressure to give the major isomer of the title compound (Isomer 1) (4.18 g, 51%) LCMS (System A) RT=1.20 min, ES+ve m/z 531 (M+H)$^+$, $[\alpha]_D^{20}$+10 (c 1.0 in EtOH), Analytical chiral HPLC on Chiralpak AD-H RT=7.2 min. Evaporation of the fractions eluting with RT=14-21 min gave the minor diastereoisomer (isomer 2) (462 mg, 6%) as a brown oil.

Intermediate 8: (S)-tert-Butyl 3-(3-morpholinophenyl)-4-((R)-3-(2-(5, 6, 7, 8-tetrahydro-1, 8-naphthyridin-2-yl) ethyl) pyrrolidin-1-yl) butanoate (Isomer 1)

A solution of tert-butyl 4-((R)-3-(2-(1,8-naphthyridin-2-yl)ethyl)pyrrolidin-1-yl)-3-(3-morpholinophenyl)butanoate (Intermediate 7, Isomer 1) (4.18 g, 7.88 mmol) was hydrogenated in EtOH (20 mL) over Pd/C (838 mg) under an atmosphere of hydrogen gas at room temperature for 60 h. The catalyst was removed by filtration through a 10 g celite cartridge and washed with ethanol. The combined filtrate and washings were evaporated in vacuo to give the title compound (3.48 g, 83%) as a brown oil. LCMS (System A) RT=1.36 min, ES+ve m/z535 (M+H)$^+$.

Intermediate 9: 4-(3-Bromophenyl)morpholine

A mixture of 1,3-dibromobenzene (3.89 mL, 32.1 mmol), morpholine (1.40 mL, 16.1 mmol), Pd$_2$(dba)$_3$ (736 mg, 0.803 mmol), sodium tert-butoxide (1.6 g, 16.6 mmol), BINAP (750 mg, 1.20 mmol) and toluene (8 mL) was placed into a microwave vial. The vial was sealed and the reaction was heated in a microwave oven (normal power, 50° C., 60 min). The reaction was cooled to ambient temperature, water was added to the reaction mixture (20 mL) and the organic layer was separated and concentrated under reduced pressure. The residue was dissolved in MeOH (20 mL) and applied to a pre-conditioned (with methanol) aminopropyl cartridge. The column was washed with MeOH (2CV), then with 2M ammonia in methanol (2 CV). The appropriate fractions were concentrated under reduced pressure to provide the title compound (2.3 g, 59%) as an orange oil: LCMS (System A) RT=1.08 min, ES+ve m/z 242/244 (M+H)$^+$.

Intermediate 10: 4-(3-Cyclopropylphenyl) morpholine 4-(3-Bromophenyl) morpholine (Intermediate 9) (3.3 g, 13.6 mmol) in THF (10 mL) was added to 0.5M cyclopropylmagnesium bromide in THF (32.7 mL, 16.4 mmol), followed by PdCl$_2$ (dppf)-CH$_2$Cl$_2$ adduct (378 mg, 0.463 mmol). The mixture was refluxed under nitrogen (70° C.) for 2 h. The reaction mixture was concentrated under vacuum and the residue was dissolved in MeOH, and applied to a pre-conditioned (with MeOH) SCX-2 cartridge. The cartridge was eluted with MeOH (2CV) and then 2M ammonia in MeOH (2CV). The appropriate fractions were collected and concentrated under reduced pressure. The residue was dissolved in DCM (5 mL) and purified by chromatography on a silica cartridge (100 g) eluting with 0-50% EtOAc-cyclohexane over 30 min. The appropriate fractions were concentrated under reduced pressure to provide the title compound (2.1 g, 76%): LCMS (System A) RT=1.08 min, ES+ve m/z 204 (M+H)$^+$.

Intermediate 11: 4-(3-Cyclopropyl-5-(4, 4, 5, 5-tetramethyl-1, 3, 2-dioxaborolan-2-yl) phenyl) morpholine A microwave vial containing 4-(3-cyclopropylphenyl) morpholine (Intermediate 10) (1.0 g, 4.9 mmol) in tert-butyl methyl ether (8 mL), bis(pinacolato)diboron (available from Aldrich) (750 mg, 2.95 mmol), 4,4'-di-tert-butyl-2,2'-bipyridine (79 mg, 0.29 mmol) and methoxy(1,5-cyclooctadiene) iridium (I) dimer (98 mg, 0.15 mmol) was heated in a microwave oven (high power) at 80° C. for 60 min. The reaction mixture was adsorbed onto florisil and purified by chromatography on three silica cartridges (100 g each) eluting with 0-50% EtOAc-cyclohexane over 60 min. The appropriate fractions were concentrated under vacuum to give the title compound (845 mg, 52%): LCMS (System A) RT=1.31 min, ES+ve m/z330 (M+H)$^+$.

Intermediate 12: (S)-tert-butyl 4-((R)-3-(2-(1, 8-naphthyridin-2-yl) ethyl) pyrrolidin-1-yl)-3-(3-cyclopropyl-5-morpholinophenyl) butanoate (R, E)-tert-butyl 4-(3-(2-(1,8-naphthyridin-2-yl)ethyl) pyrrolidin-1-yl)but-2-enoate (Intermediate 6) (300 mg, 0.816 mmol), chloro(1,5-cyclooctadiene)rhodium (I) dimer (20.13 mg, 0.041 mmol), 4-(3-cyclopropyl-5-(4,4,5,5-tetramethyl-1,3,2-dioxaborolan-2-yl)phenyl)morpholine (Intermediate 11) (605 mg, 1.84 mmol), (R)-BINAP (61 mg, 0.098 mmol) and 3.8 M KOH (0.430 mL, 1.63 mmol) were dissolved in 1,4-dioxane (2 mL) and the solution was heated in a microwave oven (high power) for 100 min at 95° C. The reaction mixture was filtered through celite, and washed with EtOAc (10 mL). The combined filtrate and washings were evaporated, the residue was dissolved in MeOH (1 mL), and purified by reverse-phase chromatography on a C18, 30 g cartridge, eluting with a gradient of 5-95% [MeCN (containing 0.1% ammonia) in 10 mM aqueous ammonium bicarbonate] (20 CV). The appropriate fractions were combined and evaporated to give the title compound as a mixture of diastereoisomers (81 mg, 17%). The product was dissolved in EtOH (1 mL) and heptane (1 mL), and the two diastereoisomers were separated using chiral HPLC on a Chiralpak AD-H column (250 mm×30 mm) eluting isocratically with 40% [EtOH (containing 0.2% v/v isopropylamine) in heptanes] over 45 min, flow rate=30 mL/min, detecting at 215 nm to give the major diastereoisomer of the title compound (Intermediate 12, Isomer 1) (S)-tert-butyl 4-((R)-3-(2-(1, 8-naphthyridin-2-yl) ethyl) pyrrolidin-1-yl)-3-(3-cyclopropyl-5-morpholinophenyl) butanoate (30 mg, 6%). Analytical chiral HPLC on Chiralpak AD-H column (250 mm×4.6 mm) eluting with 40% [(EtOH containing 0.2% v/v isopropylamine) in heptanes], flow rate=1 mL/min, detecting at 215 nm: RT=5.9 min, 98.3%; and the minor isomer (Intermediate 12, Isomer 2) (R)-tert-butyl 4-((R)-3-(2-(1, 8-naphthyridin-2-yl) ethyl) pyrrolidin-1-yl)-3-(3-cyclopropyl-5-morpholinophenyl) butanoate (5 mg, 1%): analytical chiral HPLC RT=11.6 min, >99.5%.

Intermediate 13: (S)-tert-butyl 3-(3-cyclopropyl-5-morpholinophenyl)-4-((R)-3-(2-(5, 6, 7, 8-tetrahydro-1, 8-naphthyridin-2-yl) ethyl) pyrrolidin-1-yl) butanoate was prepared by hydrogenation of Intermediate 12 Isomer 1 in a similar way to that described for Intermediate 8: LCMS (System A) RT=1.45 min, ES+ve m/z575 (M+H)$^+$.

Intermediate 14: 1-(3, 5-dibromoohenyl)-1H-pyrazole

A stirred suspension of 1,3-dibromo-5-iodobenzene (available from Fluorochem) (5.00 g, 13.8 mmol), 1H-pyrazole (1.38 mL, 20.7 mmol), copper (I) iodide (526 mg, 2.76 mmol) and caesium carbonate (9.01 g, 27.6 mmol) in acetonitrile (48 mL) was heated to reflux overnight. After cooling, the reaction mixture was filtered and concentrated in vacuo. The residue was dissolved in DCM and purified by chromatography on a silica cartridge (100 g) eluting with a gradient of 0-100% EtOAc-cyclohexane over 60 min. The appropriate fractions were combined and concentrated in vacuo to afford the title compound (3.2 g, 77%): LCMS (System A) RT=1.26 min, ES+ve m/z 301, 303, 305 (M+H)$^+$.

Intermediate 15: 4-(3-bromo-5-(1H-pyrazol-1-yl) phenyl) morpholine

A mixture of 1-(3,5-dibromophenyl)-1H-pyrazole (Intermediate 14) (1.10 g, 3.64 mmol) in toluene (70 mL), morpholine (0.346 mL, 4.01 mmol), Pd$_2$(dba)$_3$ (691 mg, 0.754 mmol), sodium tert-butoxide (350 mg, 3.64 mmol) and BINAP (739 mg, 1.19 mmol) was sealed in a microwave vial and heated at 90° C. for 2 h in a Biotage Initator microwave oven. The reaction mixture was passed through a pad of celite and was washed with water (100 mL). The organic phase was further washed with brine (50 mL). The combined organic solutions were passed through a phase separator and concentrated in vacuo. The residue was dissolved in DCM and was purified by chromatography on a silica cartridge (395 g) eluting with a gradient of 0-100% EtOAc-cyclohexane to give the title compound (561.5 mg, 50%) LCMS (System A) RT=1.07 min, ES+ve m/z308, 310 (M+H)$^+$.

Intermediate 16: 4-(3-(1H-pyrazol-1-yl)-5-(4,4,5,5-tetramethyl-1,3,2-dioxaborolan-2-yl)phenyl)morpholine A mixture of 4-(3-bromo-5-(1H-pyrazol-1-yl)phenyl) morpholine (Intermediate 15) (1.56 g, 5.07 mmol), 4,4,4', 4',5,5,5',5'-octamethyl-2,2'-bi(1,3,2-dioxaborolane) (1.93 g, 7.61 mmol), [1,1'-bis(diphenylphosphino)ferrocene]dichloropalladium (0.371 g, 0.507 mmol) and potassium acetate (1.99 g, 20.3 mmol) in DMF (20 mL) was sealed in a microwave vial and heated in a Biotage Initator microwave oven at 115° C. for 1 h. The reaction mixture was combined with the reaction mixture of another reaction carried in parallel and passed through a pad of celite and washed with EtOAc. The filtrate was washed with water (100 mL) and brine (50 mL) and then the organic solution was passed through a phase separator and concentrated in vacuo. The residue was purified by chromatography on silica eluting with a gradient of 0-100% ethyl acetate-cyclohexane (14CV) to give the title compound (4.38 g): LCMS (System C) RT=1.16 min, ES+ve m/z356 (M+H)$^+$.

Intermediate 17: (S)-tert-butyl 4-((R)-3-(2-(1,8-naphthyridin-2-yl)ethyl)pyrrolidin-1-yl)-3-(3-morpholino-5-(1H-pyrazol-1-yl)phenyl)butanoate A mixture of (R,E)-tertbutyl 4-(3-(2-(1,8-naphthyridin-2-yl)ethyl)pyrrolidin-1-yl)but-2-enoate (Intermediate 6) (500 mg, 1.361 mmol) and 4-(3-(1H-pyrazol-1-yl)-5-(4,4,5,5-tetramethyl-1,3,2-dioxaborolan-2-yl)phenyl)morpholine (Intermediate 16) (1.45 g, 4.08 mmol) in 1,4-dioxane (17 mL), 2,2'-bis(diphenylphosphino)-1,1'-binaphthalene (85 mg, 0.14 mmol), chloro(1,5-cyclooctadiene)rhodium(I) dimer (33.5 mg, 0.068 mmol) and 3.8M KOH (0.358 mL, 1.36 mmol) was sealed in a microwave vial and heated at 95° C. for 40 min in a Biotage Initator microwave oven. LCMS showed incomplete reaction. The vial was sealed and heated in a Biotage Initator at 95° C. for 2 h. LCMS was similar to the first LCMS. 3.8 M KOH (0.358 mL, 1.36 mmol) was added to the reaction mixture and the vial was heated at 95° C. for 40 min. LCMS indicated no change. Additional catalyst was added (33.5 mg, 0.068 mmol) and the vial was heated at 95° C. for 40 min. The reaction mixture was concentrated in vacuo. The residue was partitioned between DCM (25 mL) and water (50 mL). The aqueous layer was further extracted with DCM (50 mL) and the combined organic solutions were washed with brine. The organic layer was passed through a phase separator and concentrated in vacuo. The residue was purified by chromatography on an aminopropyl cartridge eluting with a gradient of 0-100% EtOAc-cyclohexane. The appropriate fractions were combined and concentrated in vacuo to afford a brown oil, which required further purification. The crude product was purified by reverse-phase HPLC on SNAP cartridge eluting with a gradient of 20-75% acetonitrile (containing 0.1% formic acid)-water (containing 0.1% formic acid) (11CV). The resulting product was a mixture of diastereoisomers, which were separated by preparative chiral HPLC on a Chiralpak AD-H column (30 mm×25 cm) eluting with 50% EtOH (containing 0.2% isopropylamine)-heptane, flow rate 40 mL/min, detecting at 215 nm collecting fractions with RT=9-11.5 min and RT=15-18 min to give the title compound Isomer 1 (S)-tert-butyl 4-((R)-3-(2-(1,8-naphthyridin-2-yl)ethyl)pyrrolidin-1-yl)-3-(3-morpholino-5-(1H-pyrazol-1-yl)phenyl)butanoate (57 mg): Analytical chiral HPLC on Chiralpak AD-H column (4.6 mm id×25 cm) eluting with 50% EtOH (containing 0.2% isopropylamine)-heptane, flow rate 1 mL/min, detecting at 215 nm RT=10.3 min, LCMS (System A) RT=1.17 min, ES+ve m/z 597 (M+H)$^+$, and Isomer 2 (R)-tert-butyl 4-((R)-3-(2-(1,8-naphthyridin-2-yl)ethyl)pyrrolidin-1-yl)-3-(3-morpholino-5-(1H-pyrazol-1-yl)phenyl)butanoate (9 mg): Analytical chiral HPLC RT=11.5 min.

Intermediate 18: (S)-tert-butyl 3-(3-morpholino-5-(1H-pyrazol-1-yl)phenyl)-4-((R)-3-(2-(5,6,7,8-tetrahydro-1,8-naphthyridin-2-yl)ethyl)pyrrolidin-1-yl)butanoate A solution of tert-butyl 4-((R)-3-(2-(1,8-naphthyridin-2-yl)ethyl)pyrrolidin-1-yl)-3-(3-morpholino-5-(1H-pyrazol-1-yl)phenyl)butanoate (Intermediate 17 Isomer 1) (98 mg, 0.164 mmol) in ethyl acetate (9 mL) was hydrogenated over Rh on carbon (1.7 mg, 0.016 mmol) at room temperature for 24 h Additional Rh/C (100 mg) was added to the reaction mixture and stirred overnight. The catalyst was removed by filtration and washed with ethyl acetate. The combined filtrate and washings were concentrated under reduced pressure to give the title compound (86 mg, 88%) as a pale yellow oil: LCMS (System A) RT=1.37 min, ES+ve m/z 601 $(M+H)^+$.

Intermediate 19:
1-(3,5-dibromophenyl)-3-methyl-1H-pyrazole

A mixture of 1,3-dibromo-5-iodobenzene (6.34 g, 17.5 mmol), 3-methyl-1H-pyrazole (2.54 mL, 31.5 mmol), caesium carbonate (11.4 g, 35.0 mmol) and copper(I) iodide (667 mg, 3.50 mmol) in MeCN (70 mL) was heated to reflux overnight. After cooling, the reaction mixture was filtered and the filtrate was concentrated in vacuo. The residue was purified by chromatography on a silica column (100 g) eluting with a gradient of 0-100% EtOAc-cyclohexane over 40 min. The appropriate fractions were combined and concentrated in vacuo to afford a brown solid, which required further separation of regioisomers. The crude product was purified by reverse-phase chromatography on KP-C18-HS (120 g) eluting with a gradient of 50-75% acetonitrile-10 mM ammonium bicarbonate in water adjusted to pH10 with ammonia solution (13CV). Appropriate fractions were combined and evaporated under reduced pressure, to give the title compound (2.8 g, 51%): $^1$H NMR δ (400 MHz, DMSO-$d_6$) 8.52 (d, J=2.5 Hz, 1H), 8.05 (d, J=1.47 Hz, 2H), 7.69 (t, J=1.5 Hz, 1H), 6.38 (d, J=2.5 Hz, 1H), 2.27 (s, 3H).

Intermediate 20: 4-(3-bromo-5-(3-methyl-1H-pyrazol-1-yl)phenyl)morpholine

A solution of 1-(3,5-dibromophenyl)-3-methyl-1H-pyrazole (Intermediate 19) (2.80 g, 8.86 mmol) in toluene (80 mL) was treated with morpholine (0.841 mL, 9.75 mmol), Pd$_2$(dba)$_3$ (1.68 g, 1.83 mmol), sodium tert-butoxide (0.852 g, 8.86 mmol) and 2,2'-bis(diphenylphosphino)-1,1'-binaphthalene (1.799 g, 2.89 mmol). The mixture was heated to reflux for 2 h and then passed through a pad of celite. The filtrate was washed with water (200 mL). The organic phase was passed through a phase separator and concentrated in vacuo. The residue was purified by chromatography on a silica cartridge (325 g) eluting with a gradient of 0-100% ethyl acetate-cyclohexane (14CV) to give the title compound (1.82 g, 64%): $^1$H NMR δ (400 MHz, DMSO-$d_6$) 8.43 (d, J 2.5 Hz, 1H), 7.40 (t, J 2 Hz, 1H), 7.30 (t, J 2 Hz, 1H), 6.96 (t, J 2 Hz, 1H), 6.32 (d, J=2 Hz, 1H), 3.83-3.65 (m, 4H), 3.17-3.26 (m, 4H), 2.25 (s, 3H).

Intermediate 21: 4-(3-(3-methyl-1H-pyrazol-1-yl)-5-(4,4,5,5-tetramethyl-1,3,2-dioxaborolan-2-yl)phenyl)morpholine was prepared from Intermediate 20 in a similar way to the method described for Intermediate 16 to give the title compound (1.48 g, 76%): LCMS (System A) RT=0.65 min ES+ve m/z 288 $(M+H)^+$ for boronic acid, and RT=1.20 ES+ve m/z 370 $(M+H)^+$ for boronate ester.

Intermediate 22: tert-butyl 4-((R)-3-(2-(1,8-naphthyridin-2-yl)ethyl)pyrrolidin-1-yl)-3-(3-(3-methyl-1H-pyrazol-1-yl)-5-morpholinophenyl)butanoate was prepared from Intermediate 6 and Intermediate 21 in a similar way to the method described for the preparation of Intermediate 17. The crude product was purified by MDAP (Method A) to give the title product (30 mg, 36%) as a diastereoisomeric mixture (preparative chiral HPLC was not performed): LCMS (System A) RT=1.21 min, 24%, ES+ve m/z 611 $(M+H)^+$, and RT=1.23 min, 76%, ES+ve m/z 611 $(M+H)^+$.

Intermediate 23: tert-butyl 3-(3-(3-methyl-1H-pyrazol-1-yl)-5-morpholinophenyl)-4-((R)-3-(2-(5,6,7,8-tetrahydro-1,8-naphthyridin-2-yl)ethyl)pyrrolidin-1-vi)butanoate was prepared by hydrogenation of Intermediate 22 (mixture of diastereoisomers) in a similar way to the method described for the preparation of Intermediate 18 to give the title compound (68 mg, 89%): LCMS (System A) RT=1.38 min, ES+ve m/z 615 $(M+H)^+$.

Intermediate 24:
1-(3,5-dibromophenyl)-3,5-dimethyl-1H-pyrazole

To a stirred solution of 3,5-dibromoaniline (2.11 g, 8.41 mmol) in acetonitrile (50 mL), cooled to 0° C. in an ice bath sulfuric acid (6.82 mL, 61.4 mmol) and sodium nitrite (0.638 g, 9.25 mmol) in water (3 mL) were slowly added to the reaction mixture and this was stirred at 0° C. for 72 h before adding (R)-5-((0.5)-1,2-dihydroxyethyl)-3,4-dihydroxyfuran-2(5H)-one (1.629 g, 9.25 mmol) in water (5 mL). This was then stirred overnight and the reaction mixture was warmed to the room temperature. The reaction mixture was then treated with pentane-2,4-dione (1.718 mL, 16.82 mmol) added in one charge. This was stirred at room temperature for 72 h and for 5 h at 80° C. The reaction was diluted with EtOAc (200 mL) and was then washed with water (100 mL), HCl (2M, 50 mL) and with water again (50 mL). The organic solution was dried over sodium sulphate and concentrated in vacuo. The residue was purified by silica gel chromatography (100-200 mesh) using a 0-10% ethyl acetate in hexane gradient. The appropriate fractions were combined and evaporated in vacuo to give the title compound (1.75 g, 62% yield) as a yellow solid. LCMS ES+ve m/z 329, 331, 333 $(M+H)^+$.

Intermediate 25: 4-(3-bromo-5-(3,5-dimethyl-1H-pyrazol-1-yl)phenyl)morpholine was prepared from Intermediate 24 in a similar way to the method described for Intermediate 20 to give the title compound (3.5 g, 78%) LCMS ES+ve m/z 336, 338 $(M+H)^+$.

Intermediate 26: 4-(3-(3,5-dimethyl-1H-pyrazol-1-yl)-5-(4,4,5,5-tetramethyl-1,3,2-dioxaborolan-2-yl)phenyl)morpholine was prepared from Intermediate 25 in a similar way to the method described for Intermediate 16 to give the title compound (4.2 g, 36%) LCMS ES+ve m/z 384 $(M+H)^+$.

Intermediate 27: tert-butyl 4-(3-(2-(1,8-naphthyridin-2-yl)ethyl)pyrrolidin-1-yl)-3-(3-(3,5-dimethyl-1H-pyrazol-1-yl)-5-morpholinophenyl)butanoate In a microwave vial, a mixture of (R,E)-tert-butyl 4-(3-(2-(1,8-naphthyridin-2-yl)ethyl)pyrrolidin-1-yl)but-2-enoate (Intermediate 6) (300 mg, 0.816 mmol) and 4-(3-(3,5-dimethyl-1H-pyrazol-1-yl)-5-(4,4,5,5-tetramethyl-1,3, 2-dioxaborolan-2-yl)phenyl)morpholine (Intermediate 26) (939 mg, 2.449 mmol) dissolved in 1,4-dioxane (4 mL) was treated with chloro(1,5-cyclooctadiene)rhodium(I) dimer (20.13 mg, 0.041 mmol), KOH (0.422 mL, 1.633 mmol) and R-BINAP (50.8 mg, 0.082 mmol). The reaction mixture was sealed and heated in Biotage Initiator at 95° C. for 2 h. After cooling, the solvent was removed in vacuo. The residue was partitioned between DCM (45 mL) and water (45 mL). Brine (30 mL) was added to the aqueous layer and this was extracted with DCM (30 mL). The combined organic solutions were dried over $MgSO_4$, filtered and concentrated in vacuo. The residue was loaded on aminopropyl (110 g) using dichloromethane and was purified by chromatography (0-100% EtOAc-cyclohexane. Appropriate fractions were combined, concentrated in vacuo and separated by chiral HPLC on a Chiralpak AD-H column (250 mm×30 mm) eluting with 10% EtOH (containing 0.2% isopropylamine)-heptane, flow rate=40 mL/min to give two isomers of the title compound.

Isomer 1 (S)-tert-butyl 4-(3-(2-(1,8-naphthyridin-2-yl)ethyl)pyrrolidin-1-yl)-3-(3-(3,5-dimethyl-1H-pyrazol-1-yl)-5-morpholinophenyl)butanoate (134 mg): $^1$H NMR (600 MHz, $CDCl_3$) 1.31 (s, 9H), 1.44 (s, 1H), 1.91-1.99 (m, 2H), 1.98-2.03 (m, 1H), 2.15-2.25 (m, 1H), 2.20-2.27 (m, 1H), 2.25-2.29 (m, 4H), 2.35-2.43 (m, 1H), 2.38-2.46 (m, 1H), 2.47-2.56 (m, 1H), 2.70-2.76 (m, 1H), 2.73-2.77 (m, 1H), 2.77-2.85 (m, 1H), 2.82 (dd, J=15.4, 5.9 Hz, 1H), 2.95-3.10 (m, 2H), 3.16-3.21 (m, 4H), 3.24-3.35 (m, 1H), 3.79-3.88 (m, 4H), 5.96 (s, 1H), 6.72 (s, 1H), 6.78 (br. s, 1H), 6.80 (s, 1H), 7.37 (d, J=8.4 Hz, 1H), 7.44 (dd, J=8.1, 4.4 Hz, 1H), 8.09 (d, J=8.4 Hz, 1H), 8.15 (dd, J=8.1, 1.8 Hz, 1H), 9.07 (dd, J=4.2, 2.0 Hz, 1H); LCMS (System C) RT=0.84 min, ES+ve m/z 625 (M+H)$^+$; Analytical chiral HPLC RT=13.7 min on a Chiralpak AD column (250 mm×4.6 mm) eluting with 15% EtOH (containing 0.2% isopropylamine)-heptane, flow-rate=1 mL/min, detecting at 235 nm;

and Isomer 2 (R)-tert-butyl 4-(3-(2-(1,8-naphthyridin-2-yl)ethyl)pyrrolidin-1-yl)-3-(3-(3,5-dimethyl-1H-pyrazol-1-yl)-5-morpholinophenyl)butanoate (31 mg): Analytical chiral HPLC RT=16.3 min on a Chiralpak AD column (250 mm×4.6 mm) eluting with 15% EtOH (containing 0.2% isopropylamine)-heptane, flow-rate=1 mL/min, detecting at 235 nm.

Intermediate 28: (S)-tert-butyl 3-(3-(3,5-dimethyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoate Isomer 1 was prepared by hydrogenation of Intermediate 27 Isomer 1 in a similar way to the method described for the preparation of Intermediate 18 to give the title compound (89 mg, 88%): LCMS (System A) RT=1.42 min, ES+ve m/z 629 (M+H)$^+$.

Intermediate 29: (R)-tert-butyl 3-(2-(5,6,7,8-tetrahydro-1,8-naphthyridin-2-yl)ethyl)pyrrolidine-1-carboxylate A solution of (R)-tert-butyl 3-(2-(1,8-naphthyridin-2-yl)ethyl)pyrrolidine-1-carboxylate (Intermediate 2) (52 g, 159 mmol) in EtOAc (1.5 L) was stirred over 5% Rh/C (32.7 g, 50% wet) under a hydrogen atmosphere at room temperature for 20 h. The reaction mixture was passed through a pad of celite and the filtrate was concentrated to afford the title compound (52.6 g, 96%): LCMS (System A) RT=1.25 min, ES+ve m/z332 (M+H)$^+$.

Intermediate 30: (R)-7-(2-(pyrrolidin-3-yl)ethyl)-1,2,3,4-tetrahydro-1,8-naphthyridine A solution of (R)-tert-butyl 3-(2-(5,6,7,8-tetrahydro-1,8-naphthyridin-2-yl)ethyl)pyrrolidine-1-carboxylate (Intermediate 29) (50.72 g, 153 mmol) was treated with HCl in 1,4-dioxane (4M, 200 mL). The reaction mixture was stirred at room temperature for 2 h and then the solvent was removed in vacuo. The residue was partitioned between water and TBME. The aqueous phase was basified with 2M NaOH solution to pH 11 and extracted with DCM (three times). The DCM solution was passed through a hydrophobic frit and the filtrate was evaporated in vacuo to afford the title compound (34.69 g, 98%) as an oil: LCMS (System A) RT=0.80 min, ES+ve m/z 232 (M+H)$^+$; $[\alpha]_D^{20}$=+6 (c=0.961 in EtOH).

Intermediate 31. (R,E)-Methyl 4-(3-(2-(5,6,7,8-tetrahydro-1,8-naphthyridin-2-yl)ethyl)pyrrolidin-1-yl)but-2-enoate (R)-7-(2-(Pyrrolidin-3-yl)ethyl)-1,2,3,4-tetrahydro-1,8-naphthyridine (Intermediate 30) (7.0 g, 30.3 mmol) was dissolved in DCM (100 mL). DIPEA (10.54 mL, 60.5 mmol) was added to the solution followed by (E)-Methyl 4-acetoxybut-2-enoate (4.79 g, 30.3 mmol) and 1,1'-bis(diphenylphosphino)ferrocene]dichloropalladium(II)-DCM [Pd(dppf)$Cl_2$] (2.471 g, 3.03 mmol) and the reaction mixture was stirred overnight at room temperature. The reaction mixture was applied to two aminopropyl SPE cartridges (100 g each) and eluted with a gradient of 0-100% EtOAc-cyclohexane the appropriate fractions were combined and concentrated in vacuo to afford the title compound (7.35 g, 64%): LCMS (System D) RT=1.07 min, ES+ve m/z330 (M+H)$^+$.

Intermediate 32. Methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate isomer 1 and Isomer 2

Potassium hydroxide (3.8M, 2.58 mL, 9.79 mmol) was added to a mixture of (R,E)-methyl 4-(3-(2-(5,6,7,8-tetrahydro-1,8-naphthyridin-2-yl)ethyl)pyrrolidin-1-yl)but-2-enoate (Intermediate 31) (2.15 g, 6.53 mmol) and 4-(3-bromo-5-(4,4,5,5-tetramethyl-1,3,2-dioxoborolan-2-yl)phenyl)morpholine (3.60 g, 9.79 mmol) (available from CombiPhos), (R)-BINAP (available from Aldrich) (0.813 g, 1.3 mmol) and chloro(1,5-cyclooctadiene)rhodium(I) dimer (available from Aldrich) (0.322 g, 0.653 mmol) in 1,4-dioxane (21.5 mL). The reaction mixture was heated at 50° C. for 2 h. After cooling, the reaction mixture was diluted with EtOAc (100 mL) and water (50 mL). The two phases were separated and the organic phase was washed with brine (50 mL), dried ($MgSO_4$), filtered and concentrated in vacuo. The residue was loaded on KP-NH cartridge (100 g) and was purified on by chromatography eluting with 0-50% EtOAc-cyclohexane. The appropriate fractions were combined and concentrated in vacuo to afford the product as a diastereoisomeric mixture (2.9 g). The mixture was separated by preparative chiral HPLC on a Chiralcel OJ-H column (30 mm×25 cm) eluting with 40% EtOH (containing 0.2% isopropylamine) in heptane (containing 0.2% isopropylamine), flow-rate 30 mL/min detecting at 215 nm collecting fractions with RT=21-23 min and RT=23-31 min the latter being the major component. Fractions were combined and evaporated in vacuo and then re-purified using the same conditions to give the two diastereoisomers of the title compound:

Isomer 1

(R)-methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate (106 mg, 3%): LCMS (System A) RT=1.42 min, ES+ve m/z 571, 573 (M+H)+; Analytical chiral HPLC: RT=17.2 min, 97% on a Chiralcel OJ-H column (4.6 mm id×25 cm) eluting with 40% EtOH (containing 0.2% isopropylamine) in heptane, flow-rate 1 mL/min, detecting at 215 nm Isomer 2

(S)-methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate (1.34 g, 34%): LCMS (System A) RT=1.42 min, ES+ve m/z 571, 573 (M+H)+; RT=20.3 min, 96.6% on a Chiralcel OJ-H column (4.6 mm id×25 cm) eluting with 40% EtOH (containing 0.2% isopropylamine) in heptane, flow-rate 1 mL/min, detecting at 215 nm.

PREPARATION OF EXAMPLES

Example 1: (S)-3-(3-Morpholinophenyl)-4-((R)-3-(2-(5,6,7,8-tetrahydro-1,8-naphthyridin-2-yl)ethyl)pyrrolidin-1-yl)butanoic acid

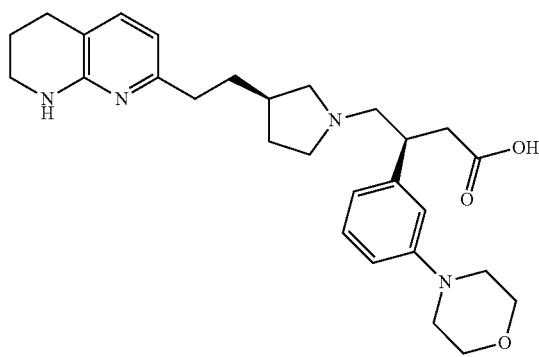 [SMILES: O=C(O)C[C@H](CN1CC[C@@H](CCc2ccc3c(n2)NCCC3)C1)c1cccc(N2CCOCC2)c1]

A solution of (S)-tert-butyl 3-(3-morpholinophenyl)-4-((R)-3-(2-(5,6,7,8-tetrahydro-1,8-naphthyridin-2-yl)ethyl)pyrrolidin-1-yl)butanoate (Intermediate 8, Isomer 1) (3.48 g, 6.51 mmol) in DCM (30 mL) was treated with trifluoroacetic acid (20 mL) and stirred at room temperature for 1.5 h. The solvent was evaporated in vacuo to give a purple oil, which was then dissolved in EtOH (10 mL) and purified on a SCX-2 cartridge (70 g), eluting with ethanol (3CV) and then 2M ammonia/methanol (3CV). The basic fractions were combined and evaporated in vacuo to give the crude product (3.175 g) as a light brown solid, which was about 96% pure. The product was further purified by reverse-phase chromatography on C18 cartridge (120 g) eluting with a gradient of 15-40% acetonitrile (containing 0.1% ammonia)-(10 mM aqueous solution of ammonium bicarbonate) over 10 column volumes. The appropriate fractions were combined and evaporated in vacuo to give the title compound (2.1 g, 67%) as a white solid: LCMS (System A) RT=0.77 min, ES+ve m/z 479 (M+H)+; 1H NMR δ (CD3OD, 400 MHz) includes 1.63-1.70 (m, 1H), 1.73-1.83 (m, 2H), 1.82-1.90 (m, 2H), 2.15-2.24 (m, 1H), 2.27-2.38 (m, 1H), 2.54 (t, J=7.8 Hz, 2H), 2.57-2.64 (m, 1H), 2.69 (t, J=6 Hz, 2H), 2.81 (dd, J=16.5, 10.5 Hz, 1H), 2.95-3.06 (m, 1H), 3.10-3.17 (m, 4H), 3.17-3.24 (m, 1H), 3.34-3.40 (m, 3H, obscured by solvent), 3.55 (dd, J=12.5, 9 Hz, 1H), 3.78-3.85 (m, 4H), 6.31-6.42 (m, 1H), 6.74 (d, J=7.5 Hz, 1H), 6.83-6.88 (m, 2H), 7.13 (d, J=7.5 Hz, 1H), 7.17-7.25 (m, 1H); $[\alpha]_D^{20}$+23 (c=1.0 in EtOH).

Example 2: (S)-3-(3-Cyclopropyl-5-morpholinophenyl)-4-((R)-3-(2-(5,6,7,8-tetrahydro-1,8-naphthyridin-2-yl)ethyl)pyrrolidin-1-yl)butanoic acid

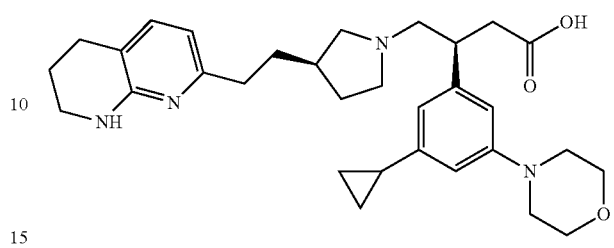

was prepared from Intermediate 12 Isomer 1 in a similar way to that described for Example 1: LCMS (System A) RT=0.88 min, ES+ve m/z519 (M+H)+; 1H NMR δ (CD3OD, 600 MHz) 7.13 (d, J=7.3 Hz, 1H), 6.63 (s, 1H), 6.57 (s, 1H), 6.48 (s, 1H), 6.38 (d, J=7.3 Hz, 1H), 3.82-3.77 (m, 4H), 3.53 (dd, J=12.7, 9.4 Hz, 1H), 3.38-3.35 (m, 3H), 3.30-3.24 (m, 3H), 3.18 (dd, J=12.7, 3.7 Hz, 1H), 3.14-3.08 (m, 4H), 3.02-2.92 (m, 1H), 2.78 (dd, J=16.3, 10.6 Hz, 1H), 2.69 (t, J=6.2 Hz, 2H), 2.60-2.56 (m, 1H), 2.56-2.51 (m, 2H), 2.32 (m, 1H), 2.23-2.14 (m, 1H), 1.89-1.83 (m, 3H), 1.83-1.72 (m, 2H), 1.67 (dq, J=13.0, 8.6 Hz), 0.96-0.85 (m, 2H), 0.71-0.62 (m, 2H).

Example 3: (S)-3-(3-morpholino-5-(1H-pyrazol-1-yl)phenyl)-4-((R)-3-(2-(5,6,7,8-tetrahydro-1,8-naphthyridin-2-yl)ethyl)pyrrolidin-1-yl)butanoic acid

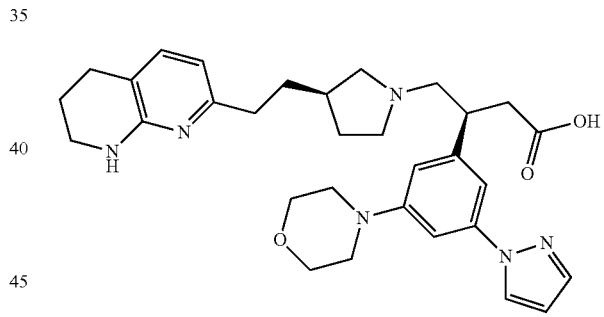

A solution of (S)-tert-butyl 3-(3-morpholino-5-(1H-pyrazol-1-yl)phenyl)-4-((R)-3-(2-(5,6,7,8-tetrahydro-1,8-naphthyridin-2-yl)ethyl)pyrrolidin-1-yl)butanoate (Intermediate 18 Isomer 1) (86.5 mg, 0.144 mmol) in DCM (6.15 mL) was treated with TFA (3 mL) and the reaction mixture was stirred at room temperature fort h. The solvent and TFA were removed in vacuo and the residue was applied to a preconditioned aminopropyl cartridge (10 g). The cartridge was washed with MeOH, and then with 2M ammonia in methanol (2.5CV). The ammoniacal fractions were concentrated in vacuo to afford the title compound (67 mg, 85%): LCMS (System D) RT=0.80 min, 98.2%, ES+ve m/z545 (M+H)+; NMR δ (500 MHz, DMSO-d6) 8.48 (1H, br s), 7.70 (1H, br s), 7.19 (1H, br s), 7.15 (1H, br s), 7.02 (1H, d, J 7 Hz), 6.78 (1H, br s), 6.51 (1H, br s), 6.30-6.24 (2H, m), 3.77-3.74 (4H, m), 3.27-3.22 (3H, m), 3.21-3.17 (4H, m), 2.88-2.68 (3H, m), 2.65-2.54 (4H, m), 2.48-2.33 (4H, m), 2.11-1.98 (1H, m), 1.97-1.87 (1H, m), 1.79-1.70 (2H, m), 1.69-1.56 (2H, m), 1.43-1.31 (1H, m).

Example 4: 3-(3-(3-methyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid

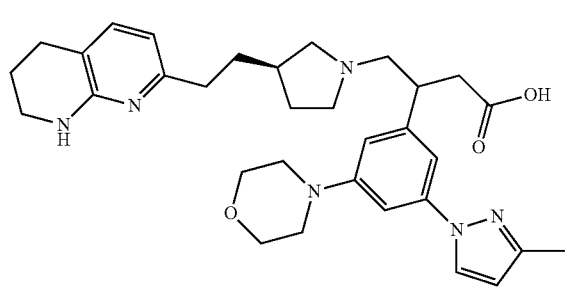 [SMILES: Cc1ccn(-c2cc(C(CC(=O)O)CN3CC[C@@H](CCc4ccc5c(n4)NCCC5)C3)cc(N3CCOCC3)c2)n1]

was obtained from Intermediate 23 (mixture of diastereoisomers) by a similar method to that described for Example 3 to give the title compound (48 mg, 88%): LCMS (System A) RT=0.83 min, ES+ve m/z 559 (M+H)+; 1H NMR δ (400 MHz, CDCl3) 7.80 (1H, d, J 2 Hz), 7.14 (1H, d, J 7.3 Hz), 7.10 (1H, m), 6.94 (1H, br s), 6.65 (1H, br s), 6.28 (1H, d, J 7.3 Hz), 6.23 (1H, d, J 2 Hz), 3.91-3.83 (4H, m), 3.52-3.35 (4H, m), 3.27-3.20 (4H, m), 3.12-2.94 (2H, m), 2.79-2.66 (5H, m), 2.62-2.41 (3H, m), 2.37 (3H, s), 2.36-2.29 (1H, br), 2.20-1.99 (4H, m), 1.95-1.81 (3H, m), 1.65-1.53 (1H, m), 1.50-1.40 (1H, m).

Example 5: (S)-3-(3-(3,5-dimethyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl) butanoic acid

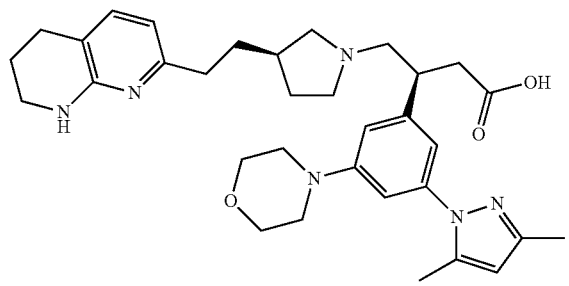 [SMILES: Cc1cc(C)n(-c2cc([C@H](CC(=O)O)CN3CC[C@@H](CCc4ccc5c(n4)NCCC5)C3)cc(N3CCOCC3)c2)n1]

was obtained from Intermediate 28 Isomer 1 by a similar method to that described for Example 3 to give the tide compound (34 mg, 62%): LCMS (System A) RT=0.85 min, ES+ve m/z 573 (M+H)+; 1H NMR δ (400 MHz, DMSO-d6) 7.03 (1H, d, J 7.3 Hz), 6.86 (1H, br s), 6.79 (1H, m), 6.75 (1H, br s), 6.37-6.32 (1H, br), 6.26 (1H, d, J 7.3 Hz), 6.03 (1H, s), 3.76-3.71 (4H, m), 3.27-3.20 (3H, m), 3.18-3.13 (4H, m), 3.00-2.57 (9H, m), 2.49-2.38 (4H, m), 2.27 (3H, s), 2.17 (3H, s), 2.11-1.88 (2H, m), 1.78-1.71 (2H, m), 1.66-1.57 (2H, m), 1.43-1.33 (1H, m).

Example 6: (S)-3-(3-Morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid

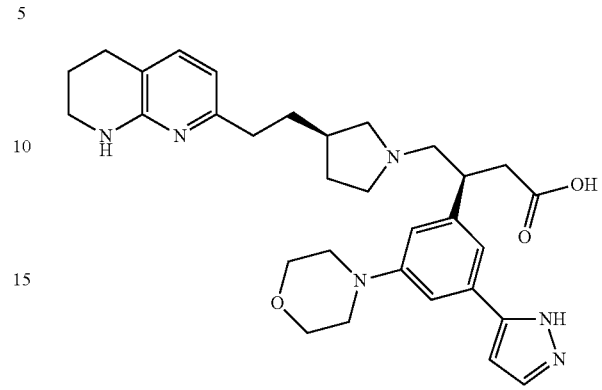

A mixture of (S)-methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate (Intermediate 32 Isomer 2) (454 mg, 0.79 mmol) 1H-pyrazole-5-boronic acid (available from Chemimpex) (267 mg, 2.39 mmol), chloro(di-2-norbornylphosphino)(2'-dimethylamino-1,1'-biphenyl-2-yl)palladium (II) (available from Fluka) (44.5 mg, 0.08 mmol), tripotassium phosphate (506 mg, 2.39 mmol) in EtOH (12.5 mL) and water (3.2 mL) was heated in a microwave reactor to 140° C. for 60 min. After cooling the reaction mixture to room temperature the mixture was combined with an identical reaction mixture of the same scale and the combined mixture was concentrated in vacuo. The residue was dissolved in DMSO-MeOH (1:1) and purified by reverse-phase chromatography on C18 (100 g column) using a gradient of 0-30% acetonitrile-0.1% aqueous ammonium bicarbonate. Appropriate fractions were evaporated in vacuo to give the tide compound (683 mg, 79%): LCMS (System D) RT=0.79 min, ES+ve m/z 545 (M+H)+; 1H NMR (DMSO-d6, 600 MHz) 14.5-12.5 (2H, br s), 7.64 (1H, br s), 7.17 (1H, s), 7.12 (1H, s), 7.01 (1H, d), 6.76 (1H, s), 6.68 (1H, d), 6.26-6.24 (2H, d+br s), 3.75 (4H, m), 3.23 (2H, m), 3.20-3.13 (5H, 2×m), 2.92 (1H, t), 2.83-2.77 (2H, m), 2.74 (1H, q), 2.59 (3H, t), 2.54 (1H, dd), 2.45-2.38 (3H, m), 2.36 (1H, t), 2.04 (1H, m), 1.92 (1H, m), 1.74 (2H, m), 1.62 (2H, m), 1.36 (1H, m).

Example 7: (S)-3-(3-(3-Methyl-1H-pyrazol-5-yl)-5-morpholinophenyl)-4-((R)-3-(2-(5,6,7,8-tetrahydro-1,8-naphthyridin-2-yl)ethyl)pyrrolidin-1-yl)butanoic acid

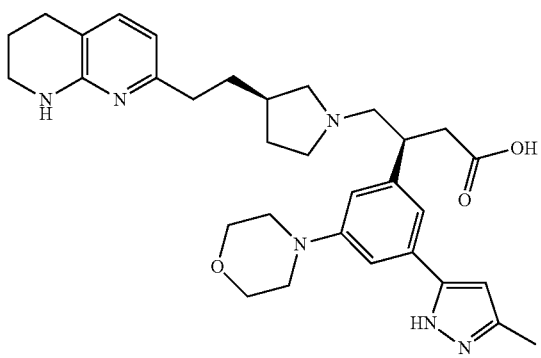 [SMILES: Cc1cc(-c2cc([C@H](CC(=O)O)CN3CC[C@@H](CCc4ccc5c(n4)NCCC5)C3)cc(N3CCOCC3)c2)[nH]n1]

A solution of (S)-methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate (Intermediate 32 Isomer 2) (57 mg, 0.100 mmol) in EtOH (0.5 mL) was added to 3-methyl-5-(4,4,5,5-tetramethyl-1,3,2-dioxaborolan-2-yl)-1H-pyrazole (available from ChemBridge) (21 mg, 0.1 mmol) in an Anton Paar microwave vial. A stock solution of tripotassium phosphate (65.5 mg, 0.308 mmol) dissolved in water (0.8 ml) was prepared, and an aliquot (0.2 mL) dispensed into the vial. Finally 2'-(dimethylamino)-2-biphenylyl-palladium(II) chloride dinorbornylphosphine complex (available from Aldrich) (5.76 mg, 10.28 μmol) was added and the reaction vessel was sealed and heated in Anton Parr microwave reactor using initial power of 600 W to 130° C. for 30 min. After cooling the reaction additional 3-methyl-5-(4,4,5,5-tetramethyl-1,3,2-dioxaborolan-2-yl)-1H-pyrazole (21 mg, 0.10 mmol) was added, followed by tripotassium phosphate (63.5 mg, 0.299 mmol) and 2'-(dimethylamino)-2-biphenylyl-palladium(II) chloride dinorbornylphosphine complex (5.59 mg, 9.97 μmol). The vial was sealed and heated for 30 min at 130° C. in the Anton Paar microwave (600 W). DMSO (0.4 mL) was added to the reaction mixture, filtered and purified by MDAP on Waters CSH C18 (19 mm×100 mm 5 μm) column using acetonitrile aqueous ammonium bicarbonate. Appropriate fractions were evaporated under a stream of nitrogen gas in a blow-down unit to give the title compound (2.8 mg, 5%): LCMS (System E) RT=0.49 min, ES+ve m/z559 (M+H)$^+$; $^1$H NMR δ (400 MHz, DMSO-d$_6$) 7.12-7.10 (m, 1H), 7.06-7.05 (m, 1H), 7.01 (d, J=7.3 Hz, 1H), 6.75-6.73 (m, 1H), 6.41 (s, 1H), 6.26-6.23 (m, 2H), 3.77-3.72 m, 4H), 3.25-3.20 (m, 2H), 3.15-3.11 (m, 4H), 2.93-2.68 (m, 4H), 2.62-2.52 (m, 5H), 2.43-2.30 (m, 5H), 2.23 (s, 3H), 2.08-1.98 (m, 1H), 1.96-1.84 (m, 1H), 1.78-1.70 (m, 2H), 1.67-1.55 (m, 2H), 1.41-1.30 (m, 1H).

Example 8. (S)-3-(3-Morpholino-5-(1H-pyrazol-4-yl)phenyl)-4-((R)-3-(2-(5,6,7,8-tetrahydro-1,8-naphthyridin-2-yl)ethyl)pyrrolidin-1-yl)butanoic acid

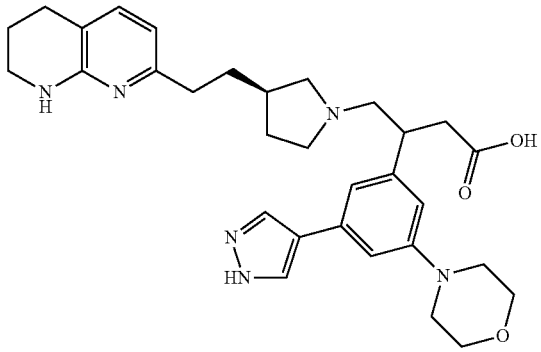 [SMILES: O=C(O)CC(CN1CC[C@@H](CCc2ccc3c(n2)NCCC3)C1)c1cc(-c2cn[nH]c2)cc(N2CCOCC2)c1]

A solution of (S)-methyl 3-(3-bromo-5-morpholinophenyl)-4-((R)-3-(2-(5,6,7,8-tetrahydro-1,8-naphthyridin-2-yl)ethyl)pyrrolidin-1-yl)butanoate (Intermediate 32 Isomer 2) (80 mg, 0.14 mmol) in EtOH (4 mL), was treated with 2'-(dimethylamino)-2-biphenylyl-palladium(II)chloride dinorbornylphosphine complex (7.84 mg, 0.014 mmol), tripotassium phosphate (89 mg, 0.42 mmol) and water (1 mL). The vial was sealed and heated in a Biotage Initiator at 130° C. for 30 min. The reaction mixture was concentrated in vacuo. The residue was loaded on a Biotage SNAP cartridge (30 g) in MeCN and was purified by reverse-phase chromatography eluting with a gradient of 25-60% MeCN (containing 0.1% ammonia) in 10 mM ammonium bicarbonate. The appropriate fractions were concentrated in vacuo to afford a pale brown solid (37.3 mg) which was further purified by MDAP (Method A). The appropriate fractions were combined and concentrated in vacuo to afford the title compound (12 mg, 16%): LCMS (System D) RT=0.77 min, 98%, ES+ve m/z 545 (M+H)$^+$; $^1$H NMR (DMSO-d$_6$, 600 MHz) 8.01 (br s, 2H), 7.01-7.02 (m, 1H), 7.01 (d, J=7.3 Hz, 1H), 6.97-6.99 (m, 1H), 6.98 (d, J=1.5 Hz, 1H), 6.93 (s, 1H), 6.64 (s, 1H), 6.25 (d, J=7.2 Hz, 2H), 3.70-3.77 (m, 4H), 3.20-3.27 (m, 3H), 3.09-3.18 (m, 5H), 2.95 (br t, J=11.2 Hz, 1H), 2.78-2.84 (m, 1H), 2.70-2.86 (m, 2H), 2.57-2.65 (m, 3H), 2.52-2.57 (m, 1H), 2.39-2.45 (m, 1H), 2.35-2.45 (m, 3H), 1.99-2.09 (m, 1H), 1.87-1.96 (m, 1H), 1.70-1.77 (m, 2H), 1.62 (br dd, J=13.2, 7.5 Hz, 2H), 1.37 (br d, J=4.4 Hz, 1H).

Example 9. (S)-2-Amino-2-oxoethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate 4-Methylbenzenesulfonic acid salt A solution of (5)-3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid (Example 6) (100 mg, 0.184 mmol) and 2-hydroxyacetamide (13.78 mg, 0.184 mmol) in DCM (2 mL) was treated with HATU (140 mg, 0.367 mmol) and DIPEA (0.071 mL, 0.404 mmol) before being stirred for 2 h at room temperature. The reaction mixture was loaded onto an aminopropyl column (10 g) and eluted with a 0-100% ethyl acetate-cyclohexane solvent system over 30 min. The appropriate fractions were combined and evaporated under reduced pressure to a colourless gum (84 mg). The reaction mixture was loaded onto another aminopropyl column (10 g) and eluted with a 0-100% (3:1 ethyl acetate-ethanol+1% NH$_3$)-cyclohexane solvent system over 20 min. The fractions were left to stand over the weekend and LCMS indicated the presence of ethyl ester. The sample was therefore re-purified using the same system and the solvent immediately evaporated from the appropriate fractions under reduced pressure to afford the free base of the title compound (36 mg, 33%) as an off white gum. LCMS (System D) RT=0.99 min, 98%, ES+ve m/z 602 (M+H)$^+$. $^1$H NMR (DMSO-d$_6$, 400 MHz) 7.66-7.61 (m, 1H), 7.17 (s, 1H), 7.01 (d, J=7.0 Hz, 1H), 6.82-6.66 (m, 2H), 6.24 (d, J=7.3 Hz, 1H), 4.31 (d, J=4.5 Hz, 2H), 3.78-3.71 (m, 5H), 3.26-3.17 (m, 3H), 3.16-3.09 (m, 3H), 2.89 (d, J=6.5 Hz, 1H), 2.75-2.64 (m, 2H), 2.43-2.34 (m, 4H), 2.17-2.10 (m, 1H), 1.77-1.70 (m, 2H), 1.54 (br. s., 1H), 1.30-1.26 (m, 1H). (S)-2-amino-2-oxoethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate (32 mg, 0.053 mmol) was dissolved in acetonitrile (1 mL) and a solution 4-methylbenzenesulfonic acid (10.12 mg, 0.053 mmol) in acetonitrile (1 mL) was added. The mixture was stirred at room temperature overnight. The solvent was blown down under nitrogen to afford the title compound (41 mg, 100%) as a white solid: LCMS (System D) RT=0.99 min, 78%, ES+ve m/z602 (M+H)$^+$. (RT=0.42 min, 20% (Tosic acid).

Example 10. (S)-2-Morpholinoethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate 4-Methylbenzenesulfonic acid salt A solution of (5)-3-(3-morpholino-5-(1H-pyrazol-5-yl)phenyl)-4-((R)-3-(2-(5,6,7,8-tetrahydro-1,8-naphthyridin-2- yl)ethyl)pyrrolidin-1-yl)butanoic acid (Example 6) (100 mg, 0.184 mmol) and 2-morpholinoethanol (24.08 mg, 0.184 mmol) in DCM (2 mL) was treated with HATU (140 mg, 0.367 mmol) and DIPEA (0.071 mL, 0.404 mmol) before being stirred for 2 h at room temperature. The reaction mixture was loaded onto an aminopropyl column (10 g) and eluted with a 0-100% ethyl acetate-cyclohexane solvent system over 30 min. The appropriate fractions were combined and evaporated under reduced pressure to give the free base of the title compound (102 mg, 84%) as a colourless gum. LCMS (System D) RT=1.07 min, 98%, ES+ve m/z 658 (M+H)$^+$. $^1$H NMR (DMSO-d$_6$, 400 MHz) 7.64 (d, J=2 Hz, 1H), 7.17 (s, 1H), 7.01 (d, J=7.3 Hz, 1H), 6.75 (s, 1H), 6.24 (d, J=7.1 Hz, 1H), 4.00 (t, J=5.8 Hz, 2H), 3.79-3.72 (m, 4H), 3.57-3.51 (m, 2H), 3.25-3.20 (m, 3H), 3.16-3.08 (m, 3H), 2.81 (s, 1H), 2.75-2.64 (m, 2H), 2.59 (t, J=5.9 Hz, 3H), 2.13 (d, J=8.6 Hz, 1H), 1.77-1.69 (m, 2H), 1.59 (d, J=7.8 Hz, 2H). (S)-2-morpholinoethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate (100 mg, 0.152 mmol) was dissolved in acetonitrile (1 mL) and 4-methylbenzenesulfonic acid (28.9 mg, 0.152 mmol) dissolved in acetonitrile (1 mL) was added. The mixture was stirred at room temperature overnight. The solvent was blown down under nitrogen to afford the title compound (94 mg, 95%) as a colourless gum. LCMS (System D) RT=1.07 min, 82%, ES+ve m/z 658 (M+H)$^+$. (RT=0.42 min, 15% (Tosic acid).

Example 11. (S)-2-(tert-Butoxy)ethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate, 4-Methyl benzenesulfonic acid salt To a stirred solution of (S)-3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid (100 mg, 0.184 mmol) (Example 6), HATU (115 mg, 0.302 mmol) and 2-(tert-butoxy)ethanol (0.072 mL, 0.551 mmol) in DCM (1 mL) was added DIPEA (0.071 mL, 0.404 mmol). The reaction mixture was stirred overnight at ambient temperature. Water (1 mL) was added and stirred for 10 min, the mixture then passed through a hydrophobic frit and the solvent evaporated in vacuo. The residue was dissolved in DMSO and purified by MDAP, using a 30-85% buffered (Method A) acetonitrile-water gradient. The appropriate fraction was taken and the solvent removed under a stream of nitrogen at room temperature. The residue (65.7 mg) was loaded onto an aminopropyl column (5 g) in DCM and purified using 0-100% ethyl acetate/cyclohexane gradient over 15 min. The appropriate fractions were combined and the solvent evaporated in vacuo to afford the free base of the title compound (61.5 mg) as a colourless glass. LCMS (System D) RT=1.27 min, 99%, ES+ve m/z645 (M+H)$^+$. The free base (50 mg) was dissolved in Acetonitrile (1 mL) and 4-methylbenzenesulfonic acid (18.07 mg, 0.095 mmol) added, the mixture was stirred overnight at room temperature. The solvent was removed in vacuo to afford the title compound (60.8 mg) as an off-white gum which solidified upon scratching of the flask. LCMS (System D) RT=1.27 min, 82%, ES+ve m/z 645 (M+H)$^+$ 0.41 min, 16% (tosic acid).

Example 12. (S)-2-Methoxyethyl 3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoate To a stirred solution of (S)-3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid (Example 6) (106 mg, 0.195 mmol), HATU (115 mg, 0.302 mmol) and 2-methoxyethanol (0.046 mL, 0.584 mmol) in DCM (1 mL) was added DIPEA (0.075 mL, 0.428 mmol). The reaction mixture was stirred for 2 h at ambient temperature. Water (1 mL) was added and stirred for 10 min, the mixture then passed through a hydrophobic frit and loaded onto an aminopropyl (10 g) column. The compound was purified by normal phase chromatography using a gradient of 0-100% ethyl acetate-cyclohexane over 15 min. The appropriate fractions were combined and the solvent removed in vacuo to afford the free base of the title compound (61.5 mg) as a colourless gum: LCMS (System D) RT=1.12 min, 100%, ES+ve m/z 603 (M+H)$^+$.

The sample was dissolved in acetonitrile (1 mL) and 4-methylbenzenesulfonic acid (19.40 mg, 0.102 mmol) added, the mixture was stirred at room temperature for 7 h. The solvent was evaporated in vacuo to afford the title compound (80.5 mg) as a colourless gum. LCMS (System D) RT=1.12 min, 75%, ES+ve m/z603 (M+H)$^+$ 0.40 min, 19%, (tosic acid).

Solubility

The Kinetic solubility was determined using an in-house assay. 5 μl of nominal 10 mM DMSO stock solutions were diluted to 100 μl with pH7.4 phosphate buffered saline (PBS), equilibrated for 1 hour at room temperature and filtered through Millipore Multiscreen$_{HTS}$-PCF filter plates (MSSL BPC). The DMSO stocks and filtrates were quantified by an in-house flow injection Chemi-Luminescent) Nitrogen Detection methodology similar to that outlined in N. Bhattachar et. al. *J. Pharm. Biomed. Anal.* 2006, 41, 152-157. All compounds were found to have a solubility in excess of 150 μM.

BIOLOGICAL ASSAYS

Cell Adhesion Assays

Reagents and methods utilised were as described [Ludbrook et al, *Biochem. J.* 2003, 369, 311), with the following points of clarification. The following cell lines were used, with ligands in brackets: K562-$\alpha_5\beta_1$ (Fibronectin), K562-$\alpha_v\beta_3$ (LAP-b$_1$), K562-$\alpha_v\beta_5$ (Vitronectin), K562-$\alpha_v\beta_6$ (LAP-b$_1$), K562-$\alpha_v\beta_8$ (LAP-b$_1$). The divalent cation used to facilitate adhesion was 2 mM MgCl$_2$. Adhesion was quantified by cell labelling with the fluorescent dye BCECF-AM (Life Technologies), where cell suspensions at 3×10$^6$ cells/mL were incubated with 0.33 mL/mL of 30 mM BCECF-AM at 37° C. for 10 minutes, before dispensing into the assay plate. At the assay conclusion cells that adhered were lysed using 50 μL/well of 0.5% Triton X-100 in H$_2$O to release fluorescence. Fluorescence intensity was detected using an Envision® plate reader (Perkin Elmer). For active inhibitors in the assay, data were fitted to a 4 parameter logistic equation for IC$_{50}$ determinations.

The mean affinities (pIC$_{50}$) of Example 1 in the Cell Adhesion Assays were, for $\alpha_v\beta_6$ pIC$_{50}$=8.4; $\alpha_v\beta_3$ pIC$_{50}$=6.2; $\alpha_v\beta_5$ pIC$_{50}$=7.3; $\alpha_v\beta_8$ pIC$_{50}$=7.8, $\alpha_v\beta_1$ pIC$_{50}$=6.6.

The mean affinities (pIC$_{50}$) of Example 2 in the cell Adhesion Assays were, for $\alpha_v\beta_6$ pIC$_{50}$=8.4; $\alpha_v\beta_3$ pIC$_{50}$=5.7; $\alpha_v\beta_5$ pIC$_{50}$=6.6; $\alpha_v\beta_8$ pIC$_{50}$=7.7.

The mean affinities (pIC$_{50}$) of Example 3 in the cell Adhesion Assays were, for $\alpha_v\beta_6$ pIC$_{50}$=8.5; $\alpha_v\beta_3$ pIC$_{50}$=5.4; $\alpha_v\beta_5$ pIC$_{50}$=6.7; $\alpha_v\beta_8$ pIC$_{50}$=7.8, $\alpha_v\beta_1$ pIC$_{50}$=7.3.

The mean affinities (pIC$_{50}$) of Example 4 in the cell Adhesion Assays were, for $\alpha_v\beta_6$ pIC$_{50}$=8.1; $\alpha_v\beta_3$ pIC$_{50}$=5.2; $\alpha_v\beta_5$ pIC$_{50}$=6.8; $\alpha_v\beta_8$ pIC$_{50}$=7.5.

The mean affinities (pIC$_{50}$) of Example 5 in the cell Adhesion Assays were, for α$_v$β$_6$ pIC$_{50}$=8.1; α$_v$β$_3$ pIC$_{50}$=5.0; α$_v$β$_5$ pIC$_{50}$=5.8; α$_v$β$_8$ pIC$_{50}$=8.0.

The mean affinities (pIC$_{50}$) of Example 6 in the cell Adhesion Assays were, for α$_v$β$_6$ pIC$_{50}$=8.5; α$_v$β$_3$ pIC$_{50}$=5.9; α$_v$β$_5$ pIC$_{50}$=7.3; α$_v$β$_8$ pIC$_{50}$=8.1, α$_v$β$_1$ pIC$_{50}$=8.0.

The mean affinities (pIC$_{50}$) of Example 7 in the cell Adhesion Assays were, for α$_v$β$_6$ pIC$_{50}$=8.0; α$_v$β$_3$ pIC$_{50}$=5.7; α$_v$β$_5$ pIC$_{50}$=6.7; α$_v$β$_8$ pIC$_{50}$=7.6.

The mean affinities (pIC$_{50}$) of Example 8 in the cell Adhesion Assays were, for α$_v$β$_6$ pIC$_{50}$=8.3; α$_v$β$_3$ pIC$_{50}$=5.4; α$_v$β$_5$ pIC$_{50}$=7.2; α$_v$β$_8$ pIC$_{50}$=8.3.

The invention claimed is:

1. A compound according to formula (I):

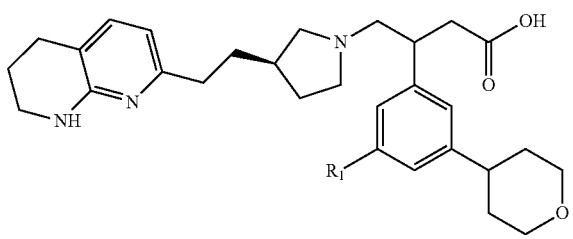

wherein R$_1$ is hydrogen, cyclopropyl, or pyrazolyl, wherein said pyrazolyl is optionally substituted by one or two methyl groups;
or a pharmaceutically acceptable salt thereof.

2. The compound according to claim 1 represented by formula (IA):

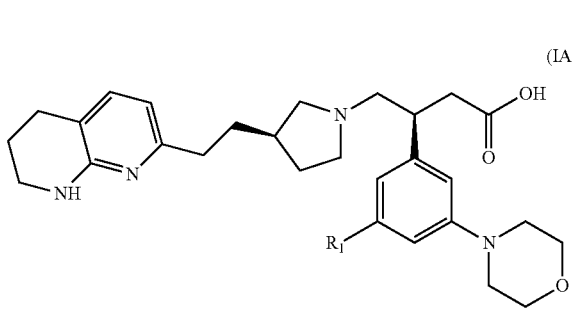

or a pharmaceutically acceptable salt thereof.

3. The compound according to claim 1, wherein R$_1$ is cyclopropyl; or a pharmaceutically acceptable salt thereof.

4. The compound according to claim 1, wherein R$_1$ is 1H-pyrazolyl; or a pharmaceutically acceptable salt thereof.

5. The compound according to claim 1, wherein R$_1$ is 3-methyl-1H-pyrazolyl; or a pharmaceutically acceptable salt thereof.

6. The compound according to claim 1, wherein R$_1$ represents a 3,5-dimethyl-1H-pyrazolyl; or a pharmaceutically acceptable salt thereof.

7. The compound according to claim 1 which is:

3-(3-morpholinophenyl)-4-((R)-3-(2-(5,6,7,8-tetrahydro-1,8-naphthyridin-2-yl)ethyl)pyrrolidin-1-yl)butanoic acid

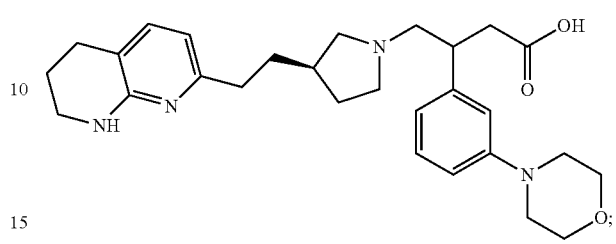

3-(3-cyclopropyl-5-morpholinophenyl)-4-((R)-3-(2-(5,6,7,8-tetrahydro-1,8-naphthyridin-2-yl)ethyl)pyrrolidin-1-yl)butanoic acid

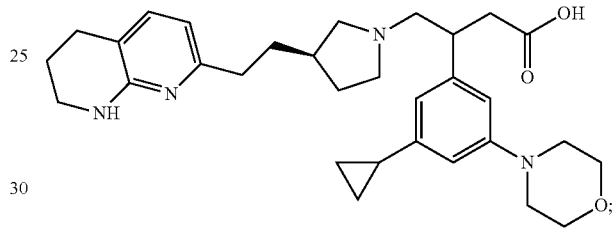

3-(3-morpholino-5-(1H-pyrazol-1-yl)phenyl)-4-((R)-3-(2-(5,6,7,8-tetrahydro-1,8-naphthyridin-2-yl)ethyl)pyrrolidin-1-yl)butanoic acid

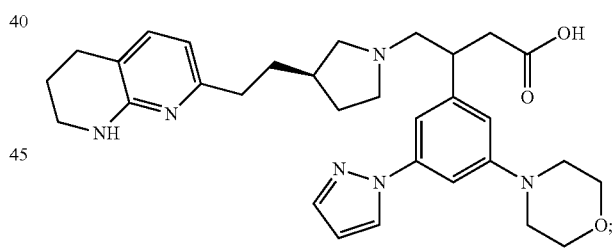

3-(3-(3-methyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid

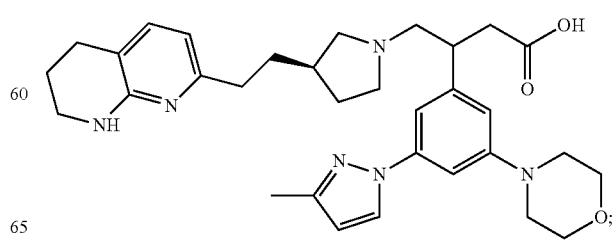

3-(3-(3,5-dimethyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid

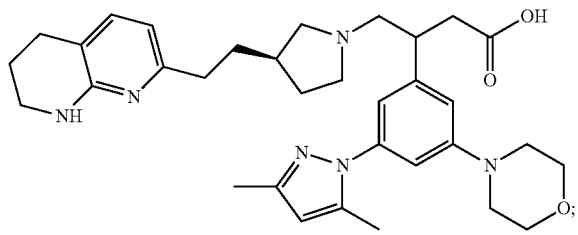

3-(3-morpholino-5-(1H-pyrazol-5-yl)phenyl)-4-((R)-3-(2-(5,6,7,8-tetrahydro-1,8-naphthyridin-2-yl)ethyl)pyrrolidin-1-yl)butanoic acid

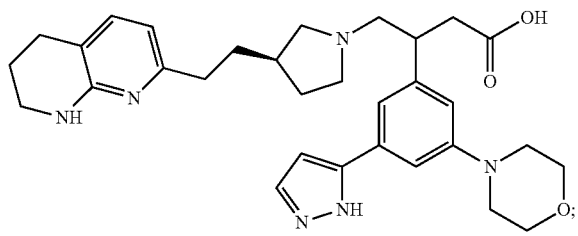 [SMILES: O=C(O)CC(CN1CC[C@@H](CCc2ccc3c(n2)NCCC3)C1)c1cc(-c2ccn[nH]2)cc(N2CCOCC2)c1]

3-(3-(3-methyl-1H-pyrazol-5-yl)-5-morpholinophenyl)-4-((R)-3-(2-(5,6,7,8-tetrahydro-1,8-naphthyridin-2-yl)ethyl)pyrrolidin-1-yl)butanoic acid

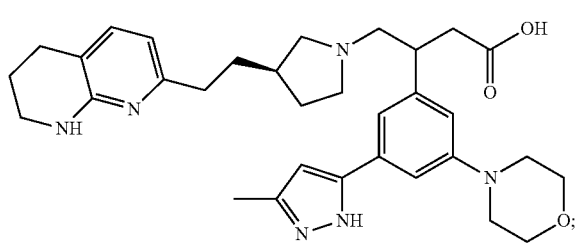 [SMILES: Cc1cc(-c2cc(C(CC(=O)O)CN3CC[C@@H](CCc4ccc5c(n4)NCCC5)C3)cc(N3CCOCC3)c2)[nH]n1]

or
3-(3-morpholino-5-(1H-pyrazol-4-yl)phenyl)-4-((R)-3-(2-(5,6,7,8-tetrahydro-1,8-naphthyridin-2-yl)ethyl)pyrrolidin-1-yl)butanoic acid

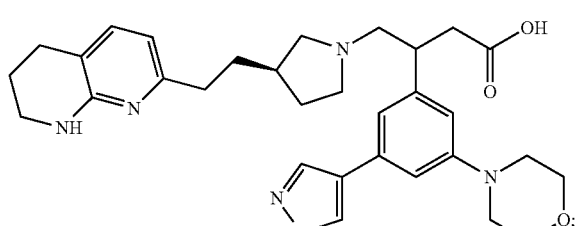

or a pharmaceutically acceptable salt thereof.

8. The compound according to claim 1 which is 3-(3-morpholinophenyl)-4-((R)-3-(2-(5,6,7,8-tetrahydro-1,8-naphthyridin-2-yl)ethyl)pyrrolidin-1-yl)butanoic acid

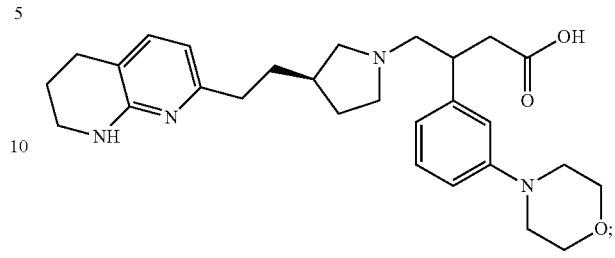

or a pharmaceutically acceptable salt thereof.

9. The compound according to claim 1 which is (S)-3-(3-morpholinophenyl)-4-((R)-3-(2-(5,6,7,8-tetrahydro-1,8-naphthyridin-2-yl)ethyl)pyrrolidin-1-yl)butanoic acid

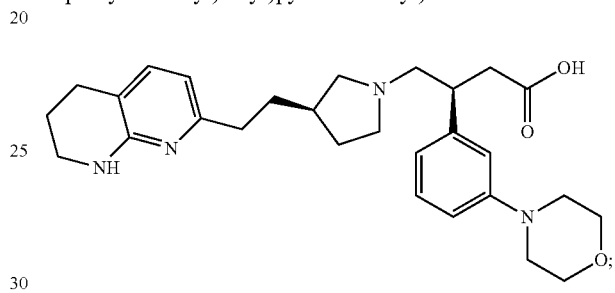

or a pharmaceutically acceptable salt thereof.

10. The compound according to claim 1 which is (R)-3-(3-morpholinophenyl)-4-((R)-3-(2-(5,6,7,8-tetrahydro-1,8-naphthyridin-2-yl)ethyl)pyrrolidin-1-yl)butanoic acid

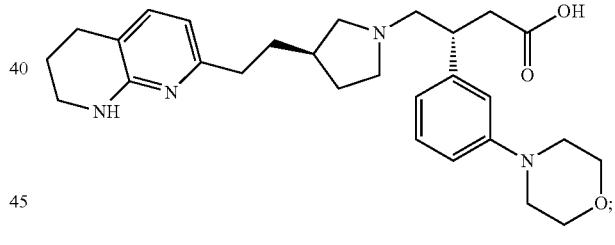

or a pharmaceutically acceptable salt thereof.

11. The compound according to claim 1 which is 3-(3-(3,5-dimethyl-1H-pyrazol-1-yl)-5-morpholinophenyl)-4-((R)-3-(2-(5,6,7,8-tetrahydro-1,8-naphthyridin-2-yl)ethyl)pyrrolidin-1-yl)butanoic acid:

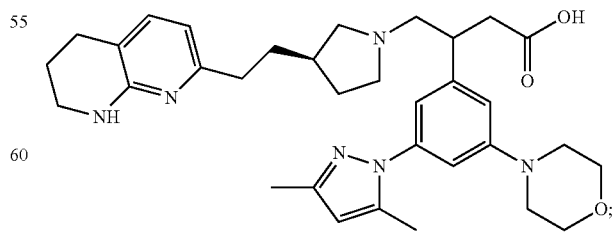

or a pharmaceutically acceptable salt thereof.

12. A method of treating a disorder in a human, wherein the disorder is responsive to antagonism of an $\alpha_v\beta_6$ receptor and is a fibrotic disease or condition, the method comprising administering to the human in need thereof a therapeutically effective amount of the compound or pharmaceutically acceptable salt according to claim 1.

13. A method of treating a disorder in a human, wherein the disorder is responsive to antagonism of an $\alpha_v\beta_6$ receptor, the method comprising administering to the human in need thereof a therapeutically effective amount of the compound or pharmaceutically acceptable salt according to claim 2.

14. The method according to claim 12, wherein the disorder is idiopathic pulmonary fibrosis.

15. The method according to claim 13, wherein the disorder is idiopathic pulmonary fibrosis.

16. A pharmaceutical composition comprising the compound or pharmaceutically acceptable salt according to claim 1, and a pharmaceutically acceptable excipient.

17. A pharmaceutical composition comprising the compound or pharmaceutically acceptable salt according to claim 2, and a pharmaceutically acceptable excipient.

\* \* \* \* \*